(12) United States Patent
Rood et al.

(10) Patent No.: US 10,588,530 B1
(45) Date of Patent: Mar. 17, 2020

(54) PHYSIOLOGICAL RECORDING DEVICE OR ELECTRODE

(71) Applicants: Aaron Rood, Rocky River, OH (US); Greg S. Shaw, Shaker Heights, OH (US); Matthew Birch, Madison, AL (US); Frederick J. Lisy, Euclid, OH (US)

(72) Inventors: Aaron Rood, Rocky River, OH (US); Greg S. Shaw, Shaker Heights, OH (US); Matthew Birch, Madison, AL (US); Frederick J. Lisy, Euclid, OH (US)

(73) Assignee: Orbital Research Inc., Cleveland, OH (US)

( * ) Notice: Subject to any disclaimer, the term of this patent is extended or adjusted under 35 U.S.C. 154(b) by 358 days.

(21) Appl. No.: 15/674,759

(22) Filed: Aug. 11, 2017

Related U.S. Application Data

(60) Continuation of application No. 13/476,496, filed on May 21, 2012, now Pat. No. 9,763,590, which is a division of application No. 11/796,902, filed on Apr. 30, 2007, now Pat. No. 8,201,330, which is a continuation-in-part of application No. 11/454,520, filed on Jun. 16, 2006, now Pat. No. 8,428,682, which is a continuation-in-part of application No. 10/988,358, filed on Nov. 12, 2004, now Pat. No. 9,326,695.

(51) Int. Cl.
*A61B 5/0408* (2006.01)
*A61B 5/0416* (2006.01)
*A61B 5/0478* (2006.01)
*A61B 5/0492* (2006.01)
*A61N 1/04* (2006.01)

(52) U.S. Cl.
CPC .......... *A61B 5/0408* (2013.01); *A61B 5/0416* (2013.01); *A61B 5/0478* (2013.01); *A61B 5/0492* (2013.01); *A61N 1/04* (2013.01)

(58) Field of Classification Search
CPC ... A61B 5/0408; A61B 5/0416; A61B 5/0478; A61B 5/0492; A61N 1/04
See application file for complete search history.

(56) References Cited

U.S. PATENT DOCUMENTS

| | | | | |
|---|---|---|---|---|
| 4,685,466 A | * | 8/1987 | Rau | A61B 5/04082 600/387 |
| 5,211,174 A | * | 5/1993 | Imran | A61B 5/0408 252/500 |

(Continued)

*Primary Examiner* — Lee S Cohen
(74) *Attorney, Agent, or Firm* — Brian Kolkowski

(57) ABSTRACT

The present invention is directed to a physiological recording device, or other types of sensors to detect a biopotential, and more particularly, a physiological recording electrode that can be used without skin preparation or the use of electrolytic gels. The invention is further directed to the configurations of structures on the physiological recording electrode's lower surface. The structures having a length, width, and height, which are capable, at least in part, of transmitting an electric potential from the skin which can be measured. The structures may or may not limit the depth of application, and/or anchor the electrode or other device during normal application, and/or allow for uniform application of the electrode or other device over unprepared skin.

20 Claims, 25 Drawing Sheets

(56) References Cited

U.S. PATENT DOCUMENTS

Figure 1:
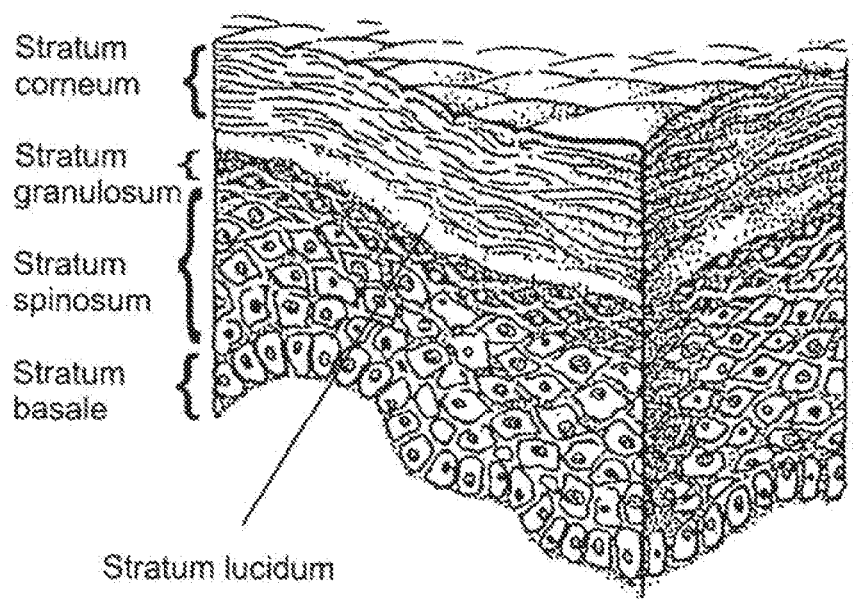

| | | | | |
|---|---|---|---|---|
| 5,305,746 A * | 4/1994 | Fendrock | ............ | A61B 5/0408 600/391 |
| 5,449,378 A * | 9/1995 | Schouenborg | ..... | A61N 1/36021 607/115 |
| 7,881,764 B1 * | 2/2011 | Schmidt | ............. | A61B 5/04025 29/825 |
| 8,032,210 B2 * | 10/2011 | Finneran | ............. | A61B 5/0492 600/382 |
| 2003/0050550 A1 * | 3/2003 | Schmidt | ............. | A61B 5/04025 600/395 |

* cited by examiner

PHYSIOLOGICAL RECORDING DEVICE OR ELECTRODE

CROSS REFERENCE TO RELATED APPLICATIONS

This application is a continuation of U.S. patent application Ser. No. 13/476,496, which was filed on May 21, 2012 and issued as U.S. Pat. No. 9,763,590, which is both a continuation-in-part of U.S. patent application Ser. No. 10/988,358, which was filed on Nov. 12, 2004 and issued as U.S. Pat. No. 9,326,695 on May 3, 2016 and a division of U.S. patent application Ser. No. 11/796,902, which was filed on Apr. 30, 2007 and issued as U.S. Pat. No. 8,201,330 on Jun. 19, 2012, which is a continuation-in-part of U.S. patent application Ser. No. 11/454,520, which was filed on Jun. 16, 2006 and issued as U.S. Pat. No. 8,428,682 on Apr. 23, 2013.

BACKGROUND OF THE INVENTION

1. Field of the Invention

The present invention is directed to a physiological recording device, or other types of sensors to detect a biopotential, and more particularly, a physiological recording electrode that can be used without skin preparation or the use of electrolytic gels. The invention is further directed to a variety of configurations of structures on the physiological recording electrode's lower surface.

2. Technical Background

Electrodes for measuring biopotential are used extensively in modern clinical and biomedical applications. These applications encompass numerous physiological tests including electrocardiography (ECG), electroencephalography (EEG), electrical impedance tomography (EIT), electromyography (EMG) and electro-oculography (EOG). The electrodes for these types of physiological tests function as a transducer by transforming the electric potentials or biopotentials within the body into an electric voltage that can be measured by conventional measurement and recording devices.

In general, most commercial physiological electrodes for these applications today are placed on the surface of the skin. Because of this it is important to understand the anatomy of the skin to understand the problems encountered with these electrodes. The skin is a layered structure, which consists of the epidermis and the dermis. The dermis contains the vascular and nervous components. Further it is the part of the skin where pain has its origins. The epidermis is an important layer in the electrode/skin interface. The epidermis consists of a number of layers as shown schematically in FIG. 1. These layers consist of:

a) Stratum basale or stratum germinativum, which contains living basal cells that grow and divide, eventually migrating into the other layers of the epidermis;

b) Stratum spinosum, which contains living cells that have migrated from the stratum basale. The early stages of desmosomes can be found in this layer;

c) Stratum granulosum, which contains cells with many desmosomal connections, forms a waterproof barrier that prevents fluid loss from the body;

d) Stratum lucidum, which is a transition layer between the stratum granulosum and the stratum corneum. It is thickest in high friction areas such as the palms and the soles of the feet; and e) Stratum corneum, which is the outer layer, contains dry, dead cells, flattened to form a relatively continuous thin outer membrane of relatively continuous thin outer membrane of skin. The deeper cells of this layer still retain the desmosomal connections, but as they are pushed toward the surface by newly formed cells in the underlying layers, the junctions gradually break and the cells are lost.

The stratum corneum is the primary source of high electrical impedance. This is because dead tissue has different electrical characteristics from live tissue, and has much higher electrical impedance. Thus, this layer dramatically influences the biopotential measurements. The stratum corneum is estimated to be typically approximately one tenth the thickness of the epidermis except for the palms of the hand and the foot where this layer is much thicker. The stratum corneum, further, is very thin and uniform in most regions of the body surface ranging from 13-15 μm with a maximum of about 20 μm. If the high impedance results from the stratum corneum can be reduced, a more stable electrode will result. Therefore with existing physiological electrodes the skin must be prepared prior to application when lower impedance is required.

The most common electrode preparation methods to improve the electrode signal and avoid the high impedance effects of the stratum corneum are: 1) shaving the hair from the skin; and 2a) abrading the stratum corneum and/or 2b) using an electrolytic gel. Electrodes having or using an electrolytic gel or fluid are often referred to as—"wet" electrodes. Hair is shaved from the skin to improve the contact between the electrodes and the skin surface. The goal of the abrasion of the stratum corneum is to reduce the thickness of (or remove) the stratum corneum (and therefore its electrically insulating characteristics). Drawbacks of abrading the skin are that the abraded area regenerates dead cells fairly quickly (resulting in a limited time period for using the electrode), and if the abrasion is too deep the person can experience pain. Additionally, electrolytic gels or fluids may be applied to abraded surface to enhance the contact. Alternatively, electrolytic gels or fluids can be applied to the surface of the skin directly. The electrolytic gel, having a high concentration of conductive ions, diffuses into the stratum corneum and improves its conductivity. Drawbacks observed with the use of electrolytic gels or fluids involve the change of conductivity with time as the gels dry, discomfort (an itching sensation) at the patient's skin as a result of the gels drying, and the possibility of a rash due to an allergic reaction to the electrolytic gels.

Further drawbacks of "wet" electrodes include skin preparation and stabilization of the electrode with respect to the skin surface. This is because movement of the electrode on the surface of the skin causes the thickness of the electrolytic layer (formed by the electrolytic gels or fluids) to change resulting in false variation in the measured biopotential commonly referred to as motion artifacts. Some electrode designs have an adhesive backing to reduce the movement of the electrode on the skin surface. However, neither of these features eliminates completely the movement of the electrode with respect to the subject's skin. Another drawback is the length of time required to prepare the skin and apply the electrolytic gels or fluids prior to measurement of the biopotentials.

A less common type of physiological electrode is a non-polarizable "dry" electrode. These ceramic, high sodium ion conducting electrodes do not need an electrolytic gel before their application. The principal of the measurements from these physiological electrodes is based on a sodium ion exchange between the skin and the electrode.

The skin-electrode impedance of these type of electrodes are found to decrease as a function of application time. This is a result of perspiration being produced by the body under the electrode almost immediately after application of the electrode on the skin. Drawbacks again, however, include many of those experienced with "wet" electrodes.

Another less common type of physiological electrode is an active "dry" electrode with an amplifier. Advances in solid-state electronic technology have made it possible to record surface biopotentials utilizing electrodes that can be applied directly to the skin without abrading the skin or using an electrolytic gel. These electrodes are not based on an electrochemical electrode-electrolyte interface. Rather, these electrodes are active and contain a very high impedance-converting amplifier. By incorporating the high impedance-converting amplifier into the electrode, biopotentials can be detected with minimal or no distortion. Although these electrodes offer the advantage of not requiring some of the preparation needed with conventional electrodes, they have certain inherent disadvantages. These electrodes are bulky in size due to the additional electronics and power sources required and they are typically more expensive to produce due to the electronic assembly required. Further, these electrodes also result in motion artifacts due to poor electrode-skin contact similar to electrodes requiring electrolytic gels or fluids.

In view of the foregoing inherent disadvantages with presently available wet and dry electrodes, it has become desirable to develop an electrode that does not require skin preparation or the use of electrolytic gels and overcomes the inherent disadvantages of presently available dry electrodes.

SUMMARY OF THE INVENTION

The present invention is directed to a physiological recording device, and more particularly, a physiological recording electrode that can be used without skin preparation or the use of electrolytic gels. The invention is further directed to the shape of the physiological electrode's lower surface, as well as a variety of configurations of surface structures on the physiological recording electrode's lower surface. These surface structures have various lengths, widths, and heights, which are preferably rigid and resist breaking, and are capable, at least in part, of transmitting an electric potential from the epidermis of the skin which can be measured. The surface structures may be used: to limit the depth of application, to anchor the device, or preferably the electrode during normal application, to penetrate the skin surface, to increase skin/electrode surface contact, and/or to allow for uniform application of the electrode or other device over unprepared skin.

The physiological recording device, has an upper and a lower surface. The lower surface can take many forms. For instance, the lower surface can be flat, concave, convex, or some other unique shape. The physiological recording device can be substantially flat on its lower surface. Various embodiments of the present invention could include changes in the physiological recording device's lower surface. Whether the lower surface is perpendicular to the device's vertical axis, or sloped depends on the application. The physiological recording device can also be substantially concave on its lower surface. An example is where the lower surface is outwardly curved like a portion of the inner surface of a large sphere. The physiological recording device can also have a convex shape on its lower surface. An example is where the lower surface curves or bulges outward, like a portion of the exterior surface of a large sphere.

The lower surface of the physiological recording device is not limited to one of the aforementioned shapes, and may take on a number of other unique shapes or some combination of the shapes listed above.

The lower surface of physiological recording device of the present invention may further include a number of surface features. These surface features may take one of many forms including but not limited to ridges, columns, penetrators, anchors, epidermal stops and combinations thereof. These surface features, in general, protrude from the various shaped substrates described above. Preferably, there is at least one structure or surface feature protruding from the electrode's lower surface. One of the important functions of the configuration of surface features is to displace or move the hair, dead skin cells and/or detritus so that the surface features can better collect the electrical biopotentials generated by the body.

The ridge(s) as used in the present invention is preferably a long, narrow structure or elevation. The ridge(s) can have a variety of cross sections over a length. Examples of these cross sections include but are not limited to a square, rectangle or trapezoid, a pointed surface like that of a triangle, a domed surface like that of an arch or arc, a cross section with a concave surface between to ridge lines forming the two ridge lines, some other unique cross-section or the like. The cross section of the ridge extends for a length. The length of the ridge is preferably substantially longer than the height or width of the cross-section of the ridge. The surface of the ridge away from the substrate, when applied to the skin surface, depresses, but does not need to pierce the skin but anchors the electrode in place to prevent motion artifacts, to diplace hair, dead skin cells and/or detritus, to increase the surface area of the electrode in contact with the skin, and to be capable, in part, of transmitting an electric potential which can be measured from the surface of the skin through the ridge.

A column(s) is another type of structure or elevation that can be used in the present invention. A column(s) can have a variety of cross sections over a length. Examples of these cross sections include but are not limited to a square, rectangle or trapezoid, a pointed surface like that of a triangle, a domed surface like that of an arch or arc, a cross section with a concave surface between two points (wherein the distance from the base to either point is greatest height of the column for the cross-section), some other unique cross-section or the like. The cross section of the column like a ridge extends for a length. However, the width of the column is preferably in proportion to the height of the cross-section of the column, and more preferably shorter than the height of the column. The surface of the column away from the substrate, when applied to the skin surface, depresses, and does not easily pierce the skin but anchors the electrode in place to prevent motion artifacts, to displace hair, dead skin cells and/or detritus, to increase the surface area of the electrode in contact with the skin, and to be capable, in part, of transmitting an electric potential which can be measured from the skin through the ridge.

A penetrator(s) is also a surface feature that can be used in the present invention. The penetrator(s) is sized and shaped for piercing the stratum corneum or outer layer of the epidermis, and accessing the lower layers of the epidermis. The penetrator can take many shapes including but not limited to pyramidal, needle-like, triangular, or any other shape that can be tapered to a point or tip. The surface of the penetrator away from the substrate, when applied to the skin surface, readily pierces the skin, preferably anchors the electrode in place to prevent motion artifacts or any substantial movement, increases the surface area of the electrode in contact with the skin and lower layers of the epidermis, and is capable, in part, of transmitting an electric potential which can be measured from the skin and lower layers of the epidermis through the penetrator.

The epidermal stop(s), which can be used in the present invention is a structure or elevation. Epidermal stops are structures of a particular height with respect to the height of the penetrator(s) or other surface features so as to prevent the penetrator(s) or other surface features such as columns and ridges from penetrating into the dermis of the skin or unduly distorting the surface of the skin, respectively, where they might cause discomfort to the subject. An epidermal stop(s) may also be incorporated into a penetrator, ridge, column or like surface feature or can be a separate surface feature. The epidermal stops may, however, have any shape known to those skilled in the art that would effectively prevent the penetrator(s) from entering the dermis of the skin, or from being applied to deeply. The epidermal stops are preferably applied in an array among the penetrators, therefore further minimizing inadvertent deep penetration or over penetration by the penetrator(s) or minimizing significant distortion of the skin by other surface structures. If the epidermal stop is a separate surface feature or incorporated into another structure, preferably, the epidermal stop in combination with at least one other surface feature or two structures with incorporated epidermal stops create a detritus trough.

A detritus trough is the area interposed between adjacent surface structures or features. These troughs, when provided or naturally occurring in the design, allow for a more accurate placement of the surface features by allowing for displacement of the hair and other detritus on the skin in these troughs. Preferably, the detritus troughs are sufficient in number and size to allow for placement of the device on skin with a significant amount of hair such as for example the scalp or the chest of a male subject. Detritus troughs are created to maximize the area available for optimal device to skin contact, by improving the probability that hair and other detritus will enter the troughs and not preventing the surface features from either coming in contact with the skin or penetrating the skin. Thus detritus troughs may be parallel to one another, perpendicular to one another, or in any other orientation made to improve the contact of the device with the skin of the subject.

An anchor(s), which can be used in the present invention is a structure or elevation that stabilizes the physiological device against a subject's skin. This stabilization further preferably prevents motion artifacts in the electrophysiological signal from the device, or any substantial movement. While the anchor can also be any of the structures described above, the anchor may also serve no other purpose except to stabilize or reduce movement of the device on the subject's skin. The anchor(s) can have a variety of cross sections over a length as described above for the various surface structures.

It is understood that the physiological recording devices of the present invention may have a combination of the various surface features described above. Various specific embodiments for the present invention are described as follows: In one embodiment, the present invention includes a physiological recording device comprising a substrate having an upper and a lower surface, and at least one ridge(s) formed on the lower surface, having a length, width, and height, wherein the ridge(s) depresses or pierces the stratum corneum or outer later of the skin, and is capable of transmitting an electric potential that can be measured from the skin through the ridge(s).

In another embodiment, the present invention includes a physiological recording device comprising a substrate having an upper and a lower surface, at least one ridge(s) formed on the lower surface, and at least one penetrator wherein the penetrator is capable of depressing or piercing through the stratum corneum or outer layer of the skin, the ridge(s) pierces or depresses the stratum corneum or outer later of the skin, and both the penetrator and ridge in combination are capable, at least in part, of transmitting an electric potential that can be measured from the skin.

In another embodiment, the present invention includes a physiological recording device comprising a substrate having an upper and a lower surface, and at least one ridge formed on the lower surface, the cross section of the at least one ridge at least in part forms an arc wherein the ridge(s) depresses and/or pierces the stratum corneum or outer layer of the skin and is capable, at least in part, of transmitting an electric potential that can be measured from the skin through the ridge(s).

In another embodiment, the present invention includes a physiological recording device comprising a substrate having an upper and a lower surface, and at least one ridge formed on the lower surface, the cross section of the at least one ridge at least in part forms a trapezoid wherein the ridge(s) depresses and/or pierces the stratum corneum or outer layer of the skin, and is capable, at least in part, of transmitting an electric potential that can be measured from the skin through the ridge(s).

In another embodiment, the present invention includes a physiological recording device comprising a substrate having an upper and a lower surface, and at least one ridge formed on the lower surface, the cross section of the at least one ridge at least in part forms a triangle wherein the ridge(s) depresses and/or pierces the stratum corneum or outer layer of the skin, and is capable, at least in part, of transmitting an electric potential that can be measured from the skin through the ridge(s).

In still another embodiment, the present invention includes a physiological recording device comprising a substrate having an upper and a lower surface, and at least one ridge formed on the lower surface, the cross section of the at least one ridge at least in part forms cup-like, parabolic end comprising two outer points and an inner bowl wherein the ridge(s) depresses and/or pierces the stratum corneum or outer layer of the skin, and is capable, at least in part, of transmitting an electric potential that can be measured from the skin through the ridge(s).

In still another embodiment, the present invention includes a physiological recording device comprising a substrate having an upper and a lower surface, the lower surface of the substrate being substantially convex and at least one structure being formed on the lower surface, wherein the structure is capable, at least in part, of transmitting an electric potential that can be measured from the skin.

In still another embodiment, the present invention includes a physiological recording device comprising a substrate having an upper and a lower surface, the lower surface of the substrate being substantially concave and at least one structure being formed on the lower surface, wherein the structure is capable, at least in part, of transmitting an electric potential that can be measured from the skin.

In still another embodiment, the present invention includes a physiological recording device comprising a substrate having an upper and a lower surface, the lower surface of the substrate being substantially curved and at least two structures being formed on the lower surface, the at least two structures both having different heights and/or shapes, wherein the at least two structures are capable, at least in part, of transmitting an electric potential that can be measured from the skin.

In still another embodiment, the present invention includes a physiological recording device comprising a substrate having an upper and a lower surface, the lower surface of the substrate not being substantially convex, concave, or flat, but rather is neither uniform nor substantially symmetric, and at least two structures being formed on the lower surface, the at least two structures both having different heights and/or shapes, wherein the at least two structures are capable, at least in part, of transmitting an electric potential that can be measured from the skin.

In still another embodiment, the present invention includes a physiological recording device for measuring physiological signals from the skin of subject comprising a substrate having an upper and a lower surface, and at least one structure being formed on the lower surface, wherein the at least one structure does not readily pierce the skin of the subject, assists in anchoring the physiological recording device to the skin of the subject and is capable, at least in part, of transmitting an electric potential from the skin that can be measured.

In still another embodiment, the present invention includes a physiological recording device comprising a substrate having an upper and a lower surface, and at least one ridge formed on the lower surface, the cross section of the at least two ridges formed on the lower surface, the at least two ridges being configured to create a detritus trough to allow for displacement of hair, dead skin cells and/or detritus on a skin of a subject, wherein the at least two ridges are capable, at least in part, of transmitting an electric potential that can be measured from the skin through the ridge(s).

It is to be understood that both the foregoing general description and the following detailed description are merely exemplary of the invention, and are intended to provide an overview or framework for understanding the nature and character of the invention as it is claimed. The accompanying drawings are included to provide a further understanding of the invention, and are incorporated in and constitute a part of this specification. The drawings illustrate various embodiments of the invention, and together with the description serve to explain the principles and operation of the invention.

Additional features and advantages of the invention will be set forth in the detailed description which follows, and in part will be readily apparent to those skilled in the art from that description or recognized by practicing the invention as described herein, including the detailed description which follows, the claims, as well as the appended drawings.

BRIEF DESCRIPTIONS OF THE DRAWINGS

FIG. 1. Cross-sectional view of the epidermis layer of a person's skin.

Figure 2:
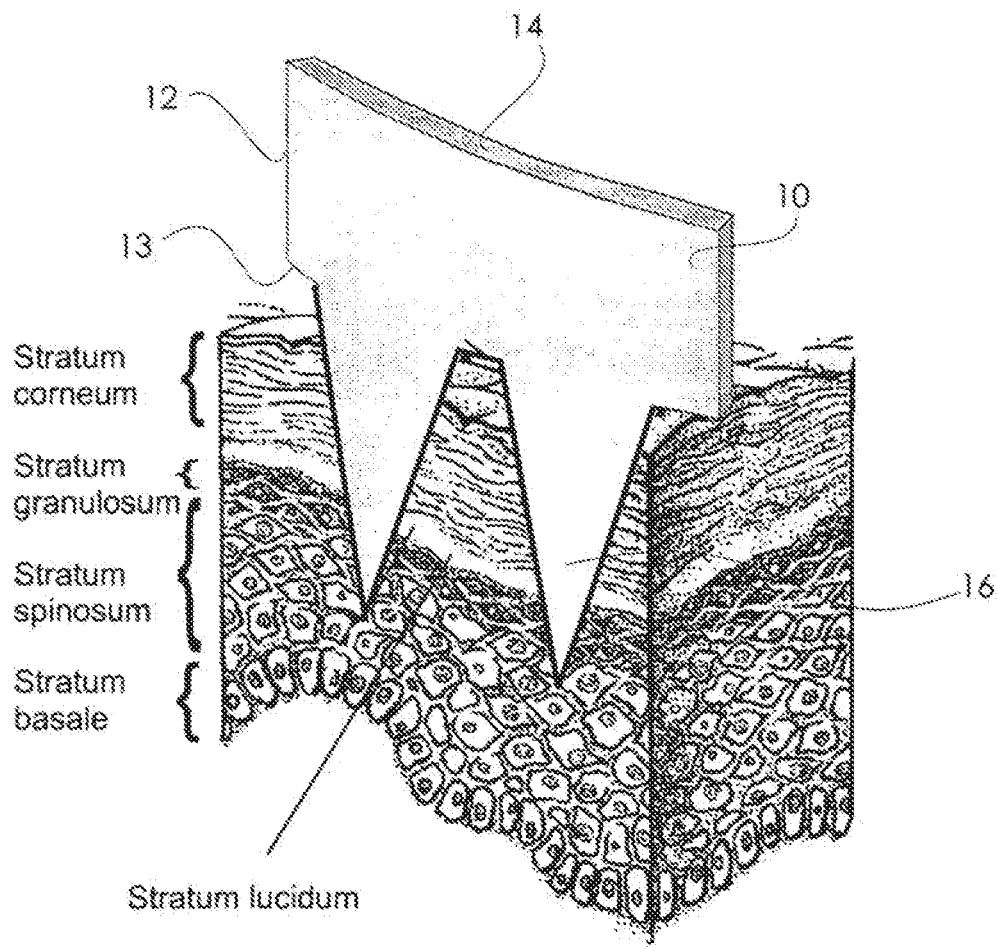

FIG. 2. Cross-sectional view of the epidermis layer and an illustration of the insertion of the penetrator(s) into the epidermis layer.

Figure 3:
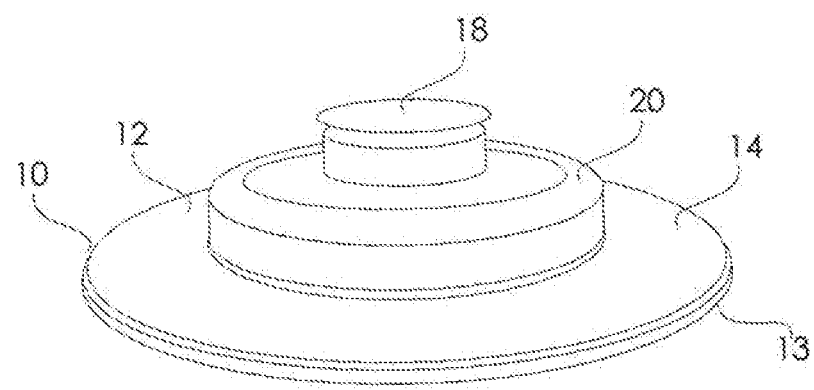

FIG. 3. Isometric view of a physiological recording electrode

Figure 4:
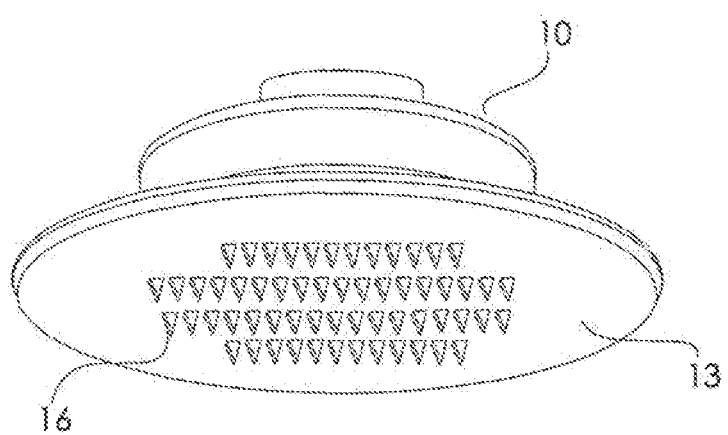

FIG. 4. Isometric view of a physiological recording electrode with penetrators on its lower surface.

Figure 5:
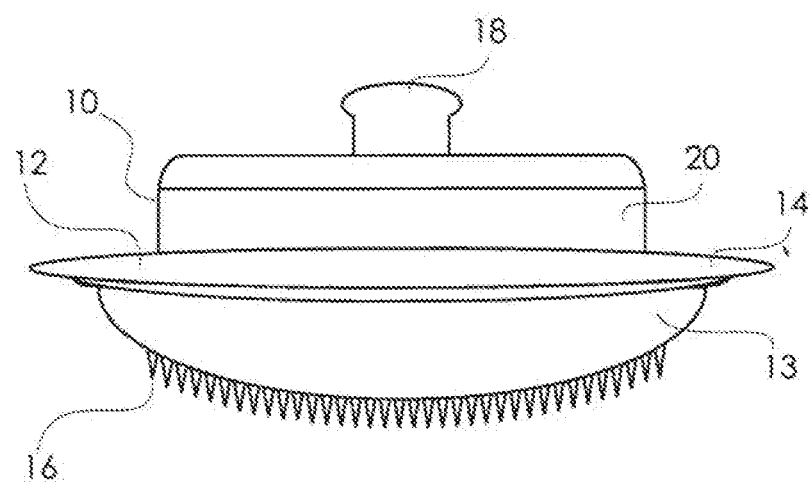

FIG. 5. Side view of a physiological recording electrode with a convex lower surface populated with penetrators that are the same height.

Figure 6:
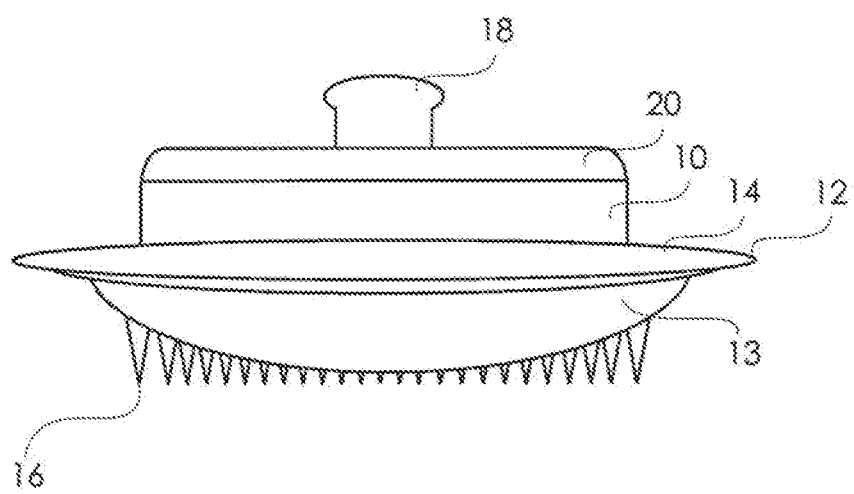

FIG. 6. Side view of a physiological recording electrode with a convex lower surface populated with penetrators that are varying in height in proportion to the curvature of the surface.

Figure 7:
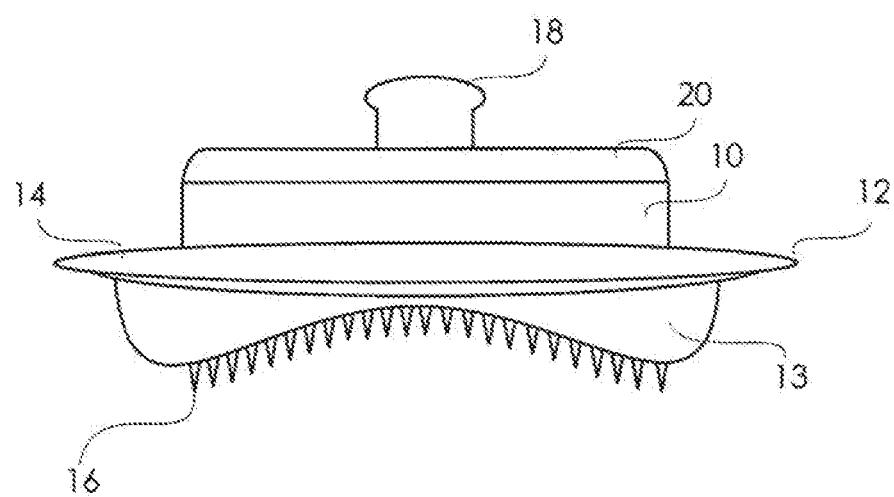

FIG. 7. Side view of a physiological recording electrode with a concave lower surface populated with penetrators that are the same height.

Figure 8:
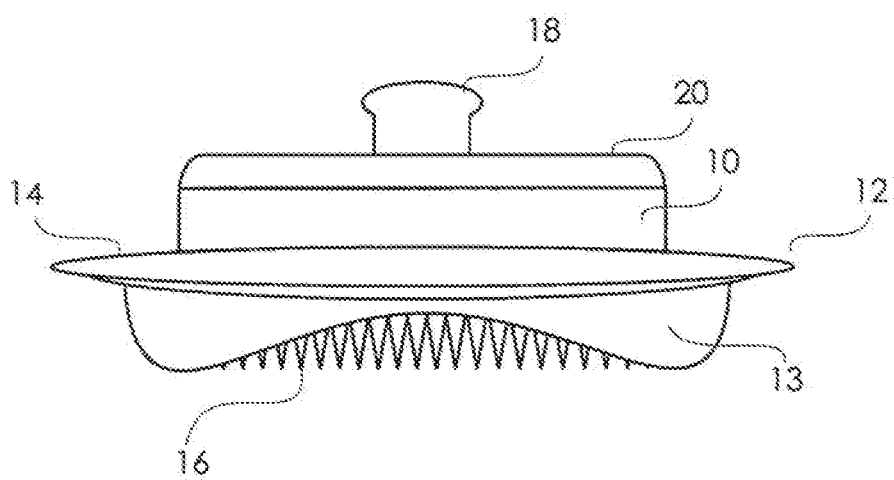

FIG. 8. Side view of a physiological recording electrode with a concave lower surface populated with penetrators that are varying in height in proportion to the curvature of the surface.

Figure 9:
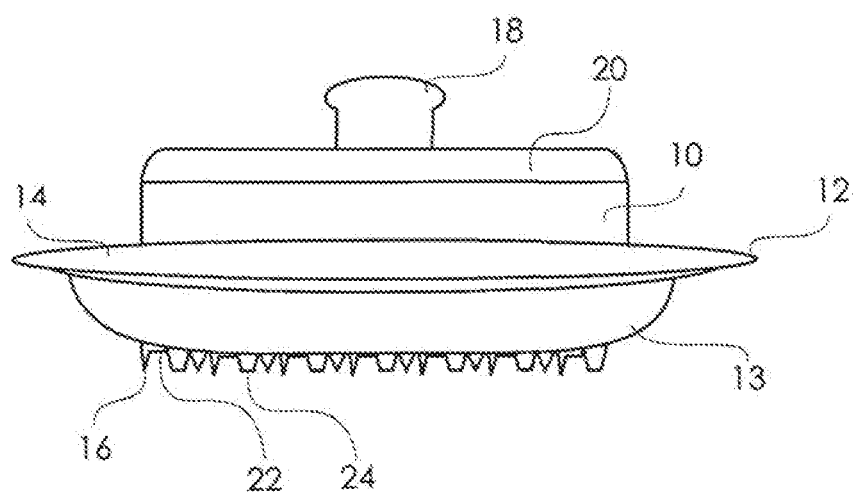

FIG. 9. Side view of a physiological recording electrode with a convex lower surface populated with penetrators and ridges that are the same height and epidermal stops that are shorter in height than the penetrators.

Figure 10:
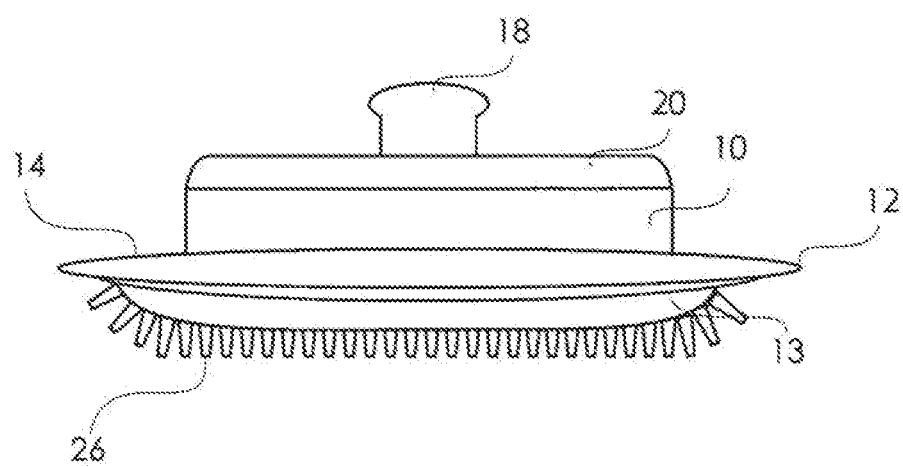

FIG. 10. Side view of a physiological recording electrode with a convex lower surface populated with ridges that are the same height, and extending out like tentacles.

Figure 11:
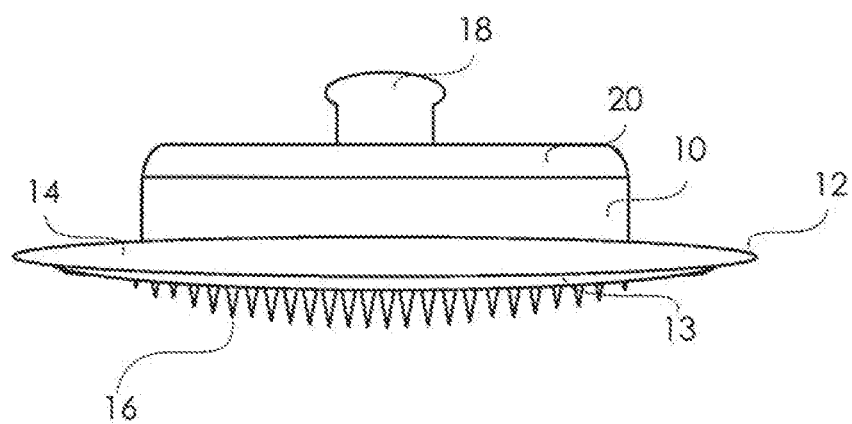

FIG. 11. Side view of a physiological recording electrode with a flat lower surface populated with penetrators that are varying in height.

Figure 12:
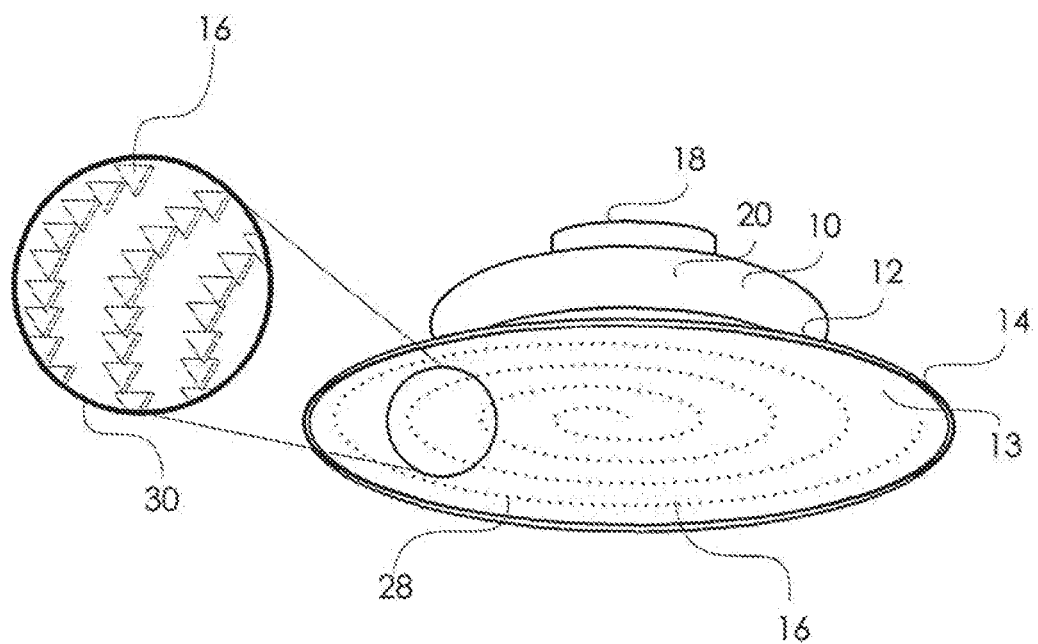

FIG. 12. Isometric view of a physiological recording electrode with penetrators on its flat lower surface arranged in a spiral.

Figure 13:
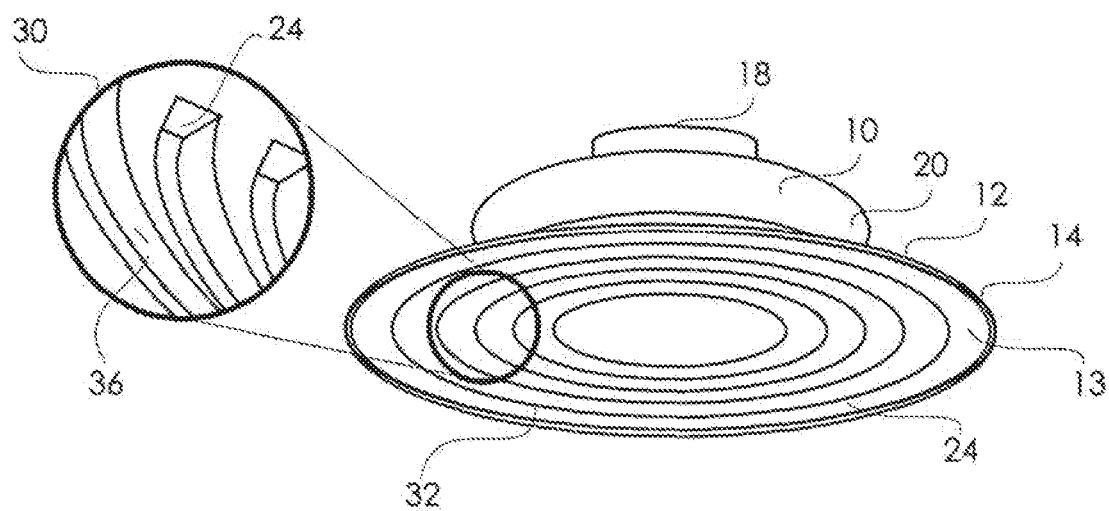

FIG. 13. Isometric view of a physiological recording electrode with trapezoidal ridges on its flat lower surface arranged in concentric rings.

Figure 14:
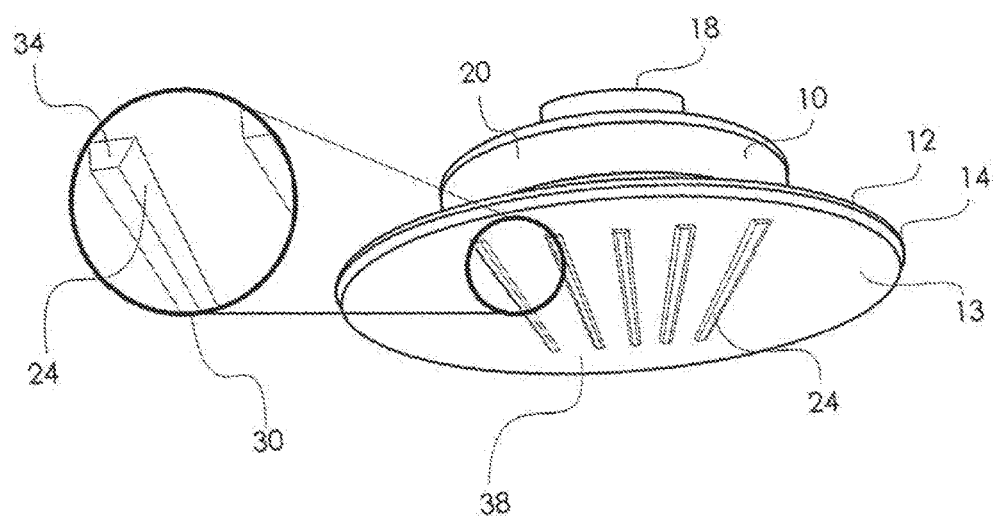
Figure 14:
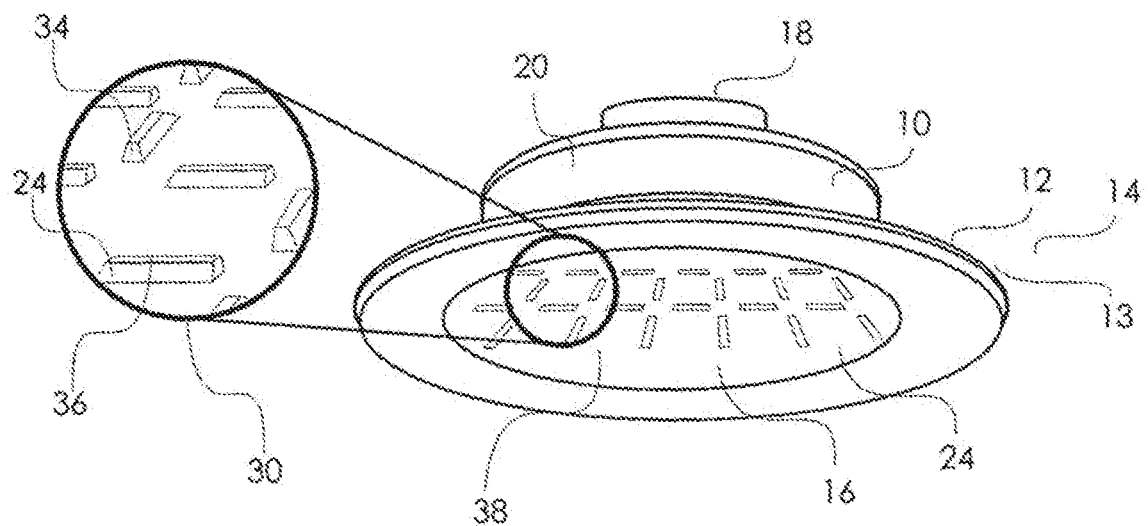

FIG. 14 a) Isometric view of a physiological recording electrode with trapezoidal ridges on its flat lower surface arranged in straight parallel lines; b) Isometric view of a physiological recording electrode with trapezoidal ridges on its flat lower surface arranged in perpendicular groupings.

Figure 15:
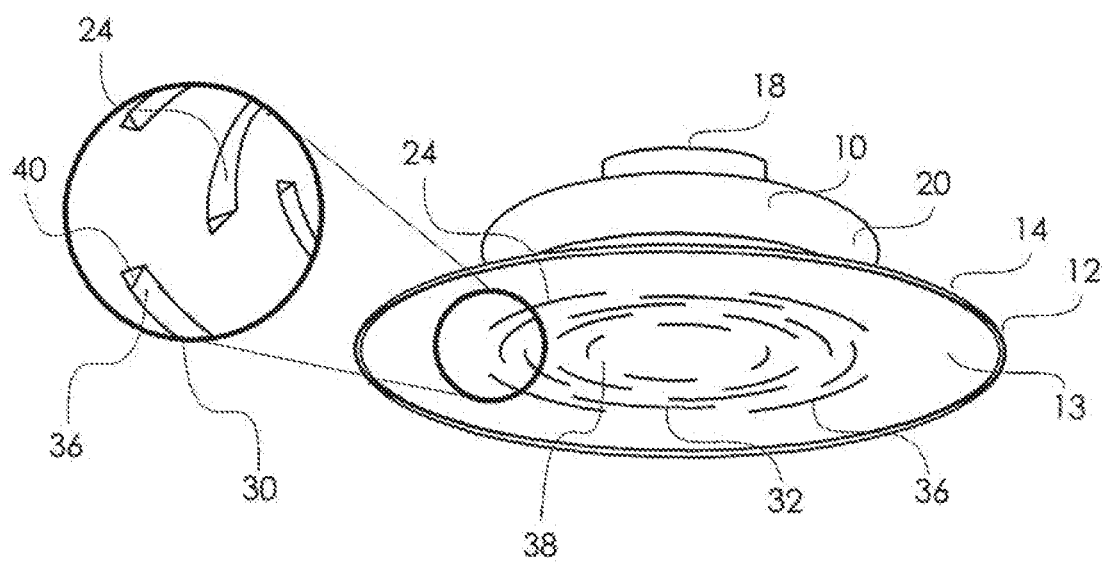

FIG. 15. Isometric view of a physiological recording electrode with triangular ridges on its flat lower surface arranged in non-continuous concentric rings.

Figure 16:
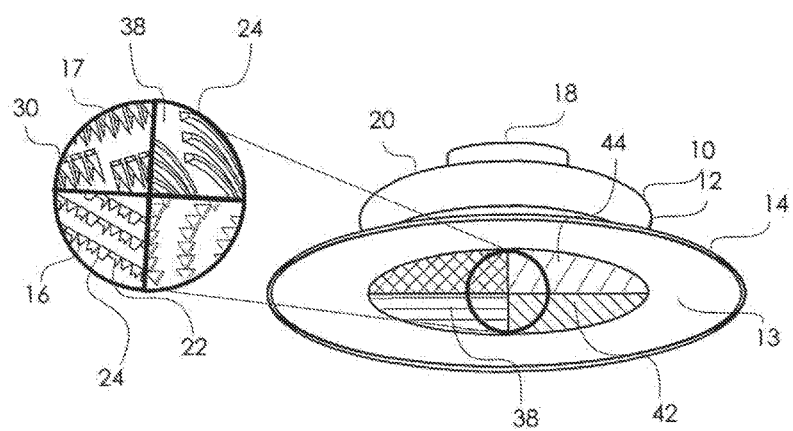

FIG. 16. Isometric view of a physiological recording electrode with four varying topographic regions have penetrators in one region, ridges in another region, thatch-like penetrators in another region, and a combination of ridges and penetrators in another region on its flat lower surface.

Figure 17:
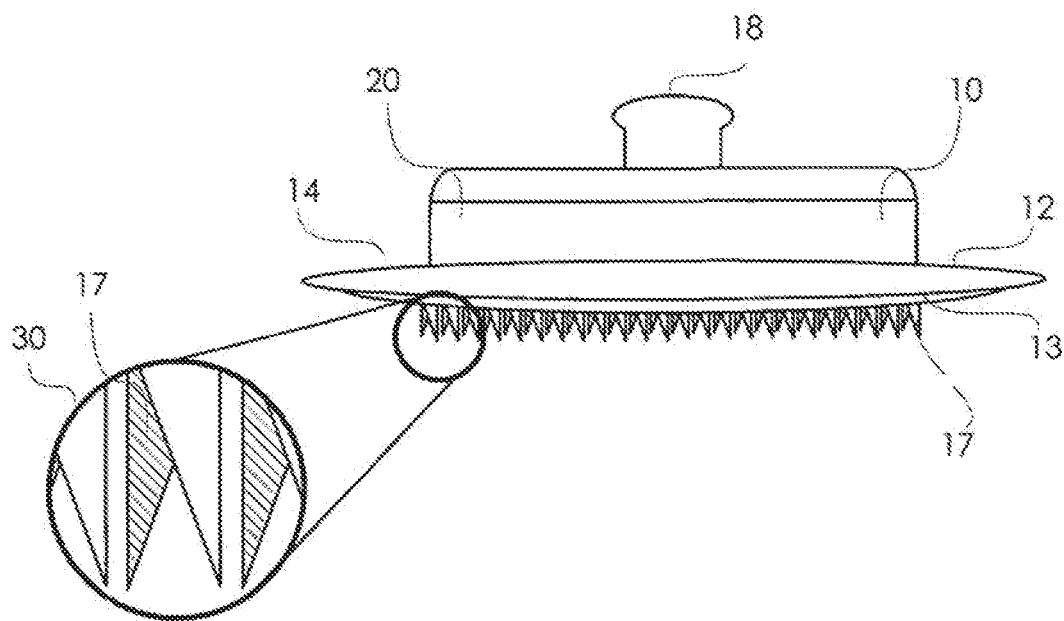

FIG. 17. Isometric view of a physiological recording electrode with penetrators on its flat lower surface arranged in a thatch-like pattern.

Figure 18:
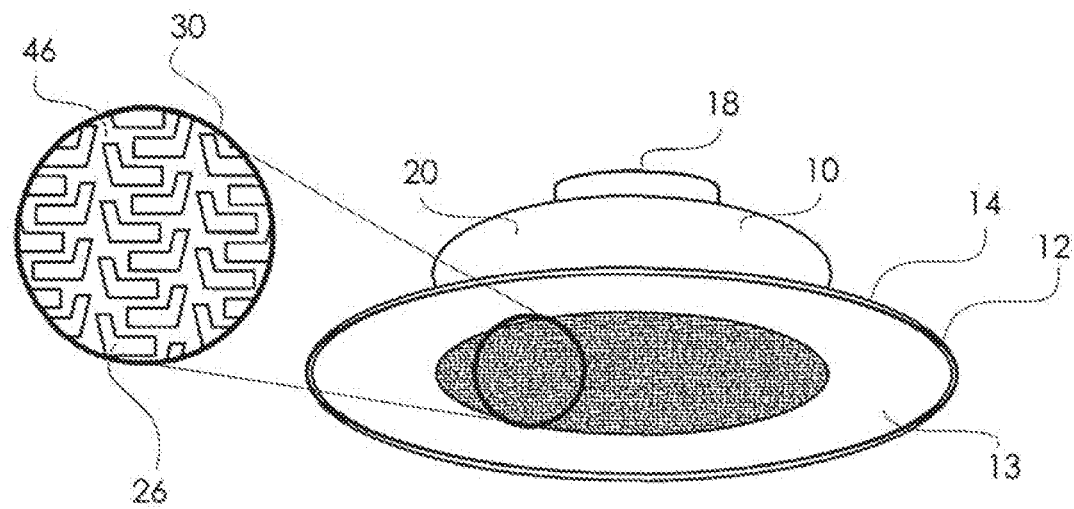

FIG. 18. Isometric view of a physiological recording electrode with interlocked columns on its flat lower surface.

Figure 19:
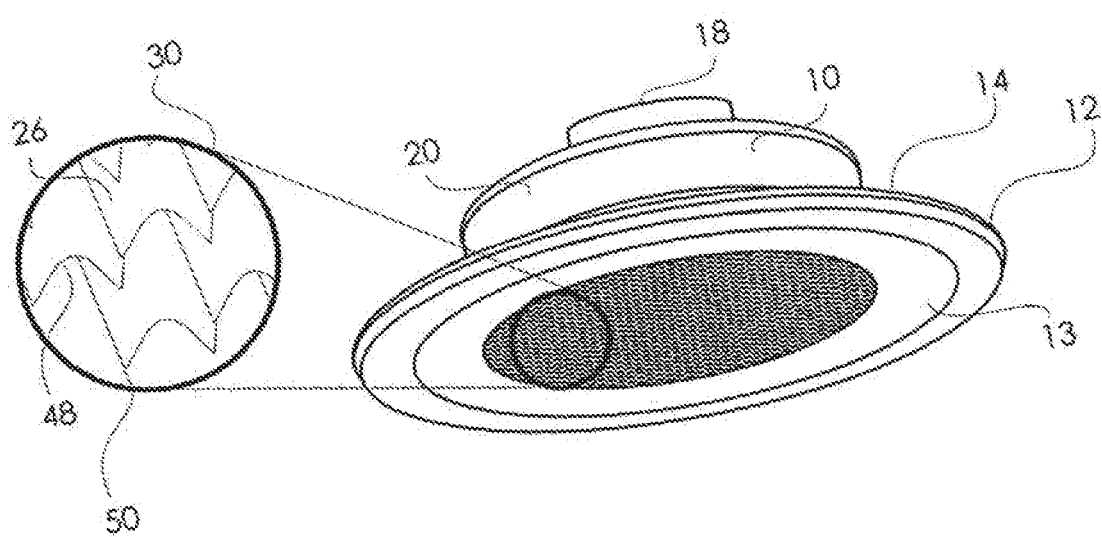

FIG. 19. Isometric view of a physiological recording electrode with cup-ended columns on its flat lower surface arranged in parallel lines.

Figure 20:
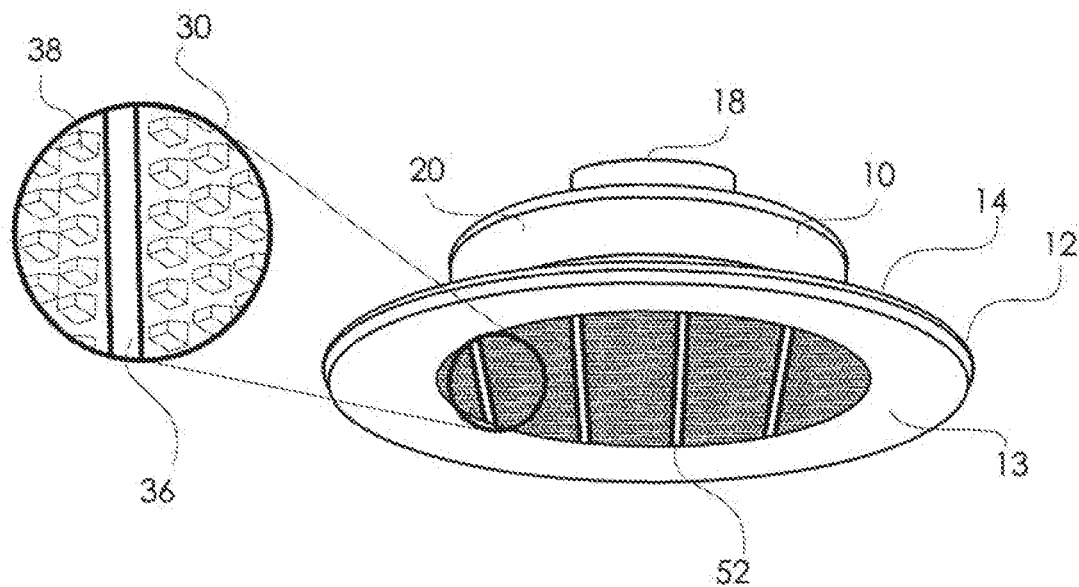

FIG. 20. Isometric view of a physiological recording electrode with trapezoidal columns on its flat lower surface arranged in clusters with channels.

Figure 21:
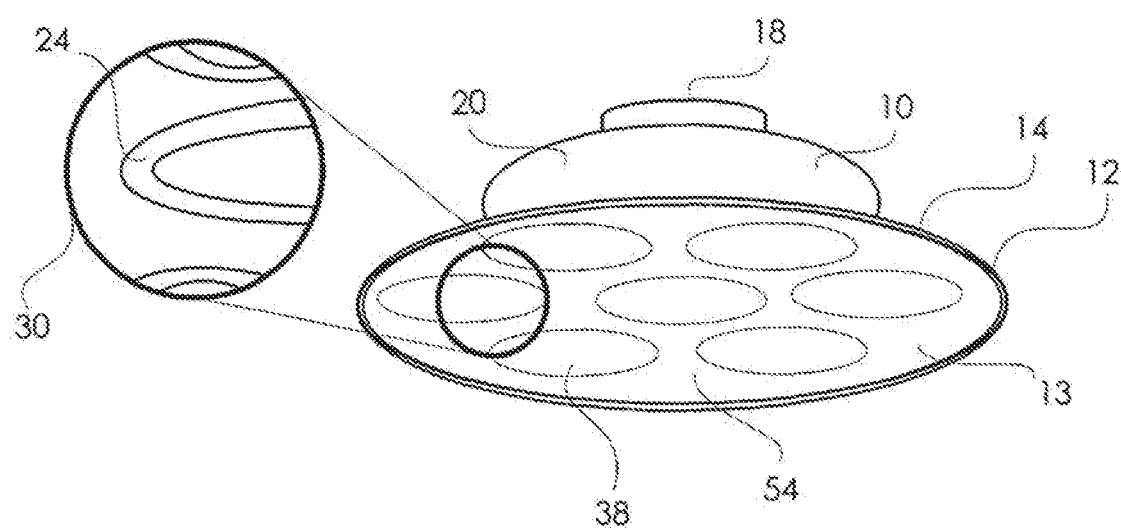

FIG. 21. Isometric view of a physiological recording electrode with triangular ridges on its flat lower surface arranged in a seven small rings.

Figure 22:
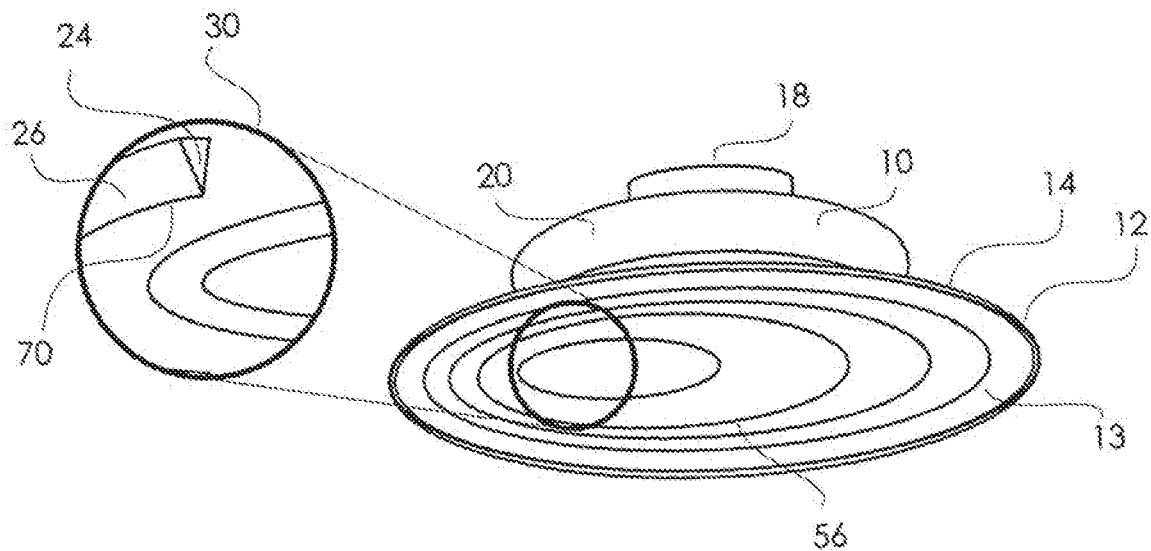

FIG. 22. Isometric view of a physiological recording electrode with triangular ridges on its flat lower surface arranged in non-concentric rings.

Figure 23:
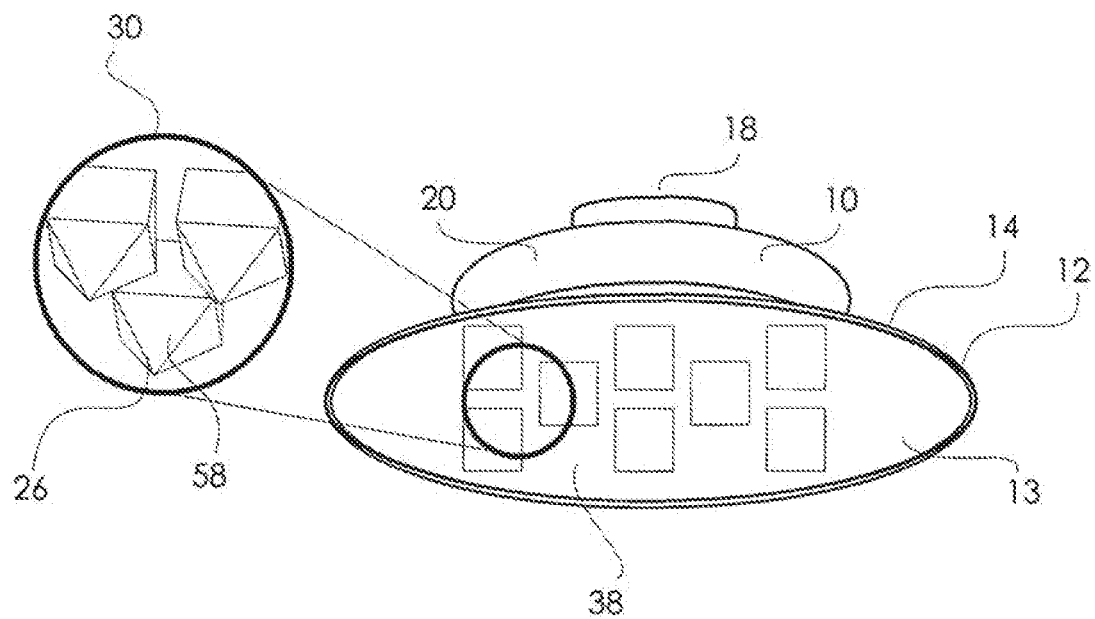

FIG. 23. Isometric view of a physiological recording electrode with pyramidal columns on its flat lower surface.

Figure 24:
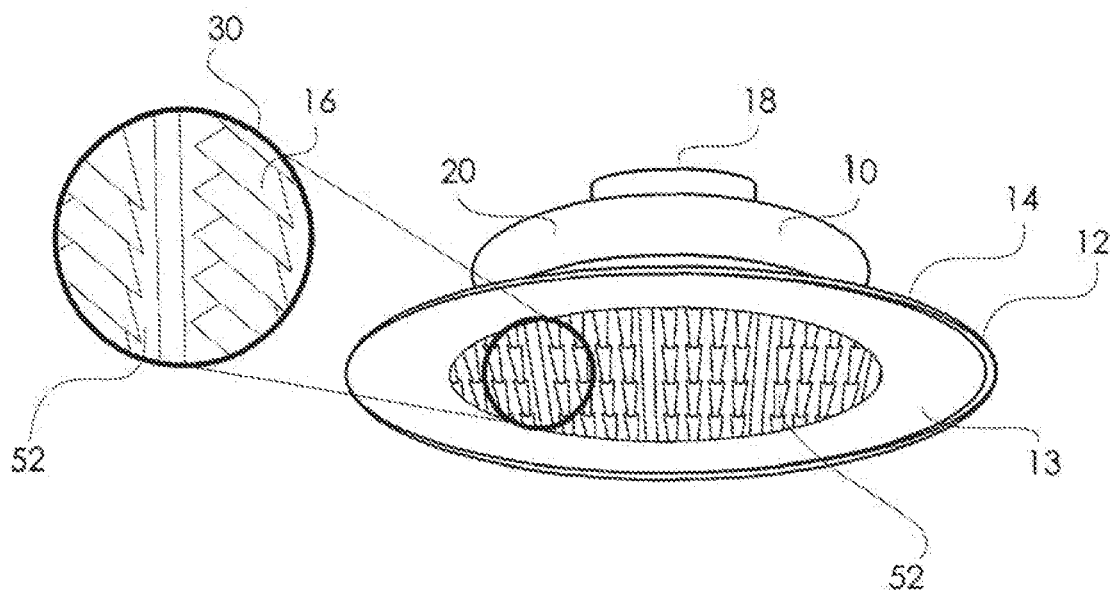

FIG. 24. Isometric view of a physiological recording electrode with penetrators on its flat lower surface arranged in clusters with channels.

DESCRIPTION OF THE PREFERRED EMBODIMENT

The present invention is related to a physiological recording device, and more particularly, a physiological recording electrode that can be used without skin preparation or with or without the use of electrolytic gels. The invention is further directed to the shape of the physiological device of the electrode's lower surface, various connection geometries, as well as a variety of configurations of surface structures on the physiological recording electrode's lower surface. These surface structures have various lengths, widths, and heights, which are preferably durable, rigid and resist breaking, and are capable, at least in part, of transmitting an electric potential from the epidermis of the skin which can be measured. The surface structures may be used to limit the depth of application, to anchor the device or preferably electrode during normal application, to penetrate the skin surface, to displace or move hair and detritus, and/or allow for uniform application of the electrode or other device over unprepared skin.

The physiological recording device or electrode, having an upper and a lower surface, can take many forms. For instance, the lower surface can be flat, concave, convex, or some other unique shape. Various embodiments of the present invention could include changes in the physiological recording device's lower surface. The physiological recording device can be substantially flat on its lower surface. Whether the lower surface is perpendicular to the device's vertical axis, or contoured depends on the application. The physiological recording device can also be substantially concave on its lower surface. An example is where the lower surface is outwardly curved like the inner surface of a sphere. The physiological recording device can also have a convex shape on its lower surface. An example is where the lower surface curves or bulges outward, like the exterior of a sphere. The lower surface of the physiological recording device is not limited to one of the aforementioned shapes, and may take on a number of other unique shapes or some combination of the shapes listed above.

The physiological recording device of the present invention may include a number of surface features, preferably elevated surface features. These elevated surface features may take one of many forms including, but not limited to, ridges, columns, penetrators, anchors, epidermal stops and combinations thereof. These surface features, in general, protrude from the various shaped substrates described above. Preferably, there is at least one structure or surface feature protruding from the electrode's lower surface.

The ridge(s) of the present invention is a long, narrow structure or elevation. Preferably, the size and shape of the ridge is such that the ridge(s) will not break during normal use, and/or will anchor the electrode to prevent motion artifacts or any substantial movement of the electrode with respect to the skin. Therefore, preferably, the appropriate aspect ratio of the height to the length of the ridge is selected to make an electrode wherein the ridge(s) will not break, and will better anchor the electrode during application. The height of the ridge(s) is measured from the edge of the ridge perpendicular to the substrate. The ridge(s), preferably, has a height from about 20 to about 1000 µm, more preferably from about 40 to about 1000 pin, even more preferably from about 100 to about 500 um, and most preferably from about 100 to about 350 um. The aspect ratio, for purposes of this invention, of the ridge is a ratio of the average height of the ridge divided by the average width of the base of the ridge. The average width of the ridge is measured by taking the width of the based of the ridge along the length and comparing it to the average height of the ridge along the length of the ridge. The ridge(s), preferably, has an aspect ratio of less than about 8:1; more preferably less than about 6:1; even more preferably less than about 4:1; still more preferably less than about 2:1; even still more preferably less than about 1.5:1; and most preferably less than about 1:1. The ridge(s), preferably, has a length to height aspect ratio. The length to height aspect ratio is the length of the ridge or its longest dimension divided by the average height of the ridge. Preferably, the length to height aspect ratio of the ridge(s) is greater than about 2:1, more preferably greater than about 4:1, even more preferably of greater than about 8:1 and most preferably of greater than about 15:1.

The ridge(s) further can have a variety of cross sections over the length. Examples of these cross sections include, but are not limited to, a square, rectangle or trapezoid, a pointed surface like that of a triangle, a domed surface like that of an arch or arc, a cross section with a concave surface between to ridge lines forming the two ridge lines, some other unique cross-section or the like. The cross section of the ridge extends for a length. The surface of the ridge away from the substrate, when applied to the skin surface, depresses, and does not readily pierce, the skin such that it anchors the electrode in place, increases the surface area of the electrode in contact with the skin, displaces or moves hair and detritus and is capable, in part, of transmitting an electric potential which can be measured from the skin through the ridge.

A column(s) is another type or form of structure or elevation that can be used in various embodiments of the present invention. Preferably, the size and shape of the column is such that the column(s) will not break during normal use, and/or will anchor the electrode to prevent motion artifacts or any substantial movement. Therefore, preferably, the appropriate aspect ratio of a column is selected to make an electrode wherein the column(s) will not break, and will better anchor the electrode during application. The height of the column(s) is measured from the edge of the ridge perpendicular to the substrate. The column(s), preferably, has a height from about 20 to about 1000 µm, more preferably from about 40 to about 800 µm, even more preferably from about 100 to about 500 um, and most preferably from about 150 to about 350 um. The aspect ratio of the column is a ratio of the average height divided by the average width of the base of the column. The column(s), preferably, has an aspect ratio of less than about 4:1, more preferably less than about 2:1, even more preferably less than about 1.5:1, and most preferably less than about 1:1. The column(s) can have a variety of cross sections over its height and width. Examples of these cross sections include but are not limited to a square, circle, rectangle or trapezoid, a pointed surface like that of a triangle, a domed surface like that of an arch or arc, a cross section with a concave surface between two points (wherein the distance from the base to either point is greatest height of the column for the cross-section), some other unique cross-section or the like, provided that the shape doesn't pierce the skin under normal conditions. The cross section of the column like a ridge extends for a length. However, the length of the column is preferably in proportion to the height of the cross-section of the column, and more preferably shorter than the height of the column. The surface of the column away from the substrate, when applied to the skin surface, depresses, and does not readily pierce, the skin such that it anchors the electrode in place, displaces or moves hair and detritus, increases the surface area of the electrode in contact with the skin, and is capable, in part, of transmitting an electric potential from the skin through the ridge which can be measured.

Penetrator(s), as used in various embodiments of the present invention, are sized and shaped for piercing or depressing the stratum corneum or outer layer of the epidermis, displacing or moving hair and detritus and accessing the lower layers of the epidermis. The penetrator can take many shapes including but not limited to pyramidal, needle-like, triangular, or any other shape that can be tapered to a point or tip. The surface of the penetrator away from the substrate, when applied to the skin surface, readily pierces or depresses the skin, preferably anchors the electrode in place to prevent motion artifacts or any substantial movement, displaces or moves hair and detritus increases the surface area of the electrode in contact with the skin and lower layers of the epidermis, and is capable, in part, of transmitting an electric potential which can be measured from the skin and lower layers of the epidermis through the penetrator.

Preferably, the penetrator(s) and other surface features are configured so as to minimize the chance of the penetrator(s) entering the dermis area of the skin thereby causing discomfort. Preferably, the size and shape of the penetrator is such that the penetrator(s) will not break during normal use, will limit the depth the penetrator enters the skin under typical application conditions, and/or will anchor the electrode to prevent motion artifacts or any substantial movement. Therefore, preferably, the appropriate aspect ratio of the height to the average width of the penetrator, contour of the edge(s) or side(s) of the penetrator, and/or height of the penetrator are selected to make an electrode wherein the penetrator(s) will not break, and will better anchor the electrode during application. The height of the penetrator(s) is measured from the tip of the penetrator perpendicular to the substrate. The penetrator(s), preferably, has a height from about 20 to about 750 µm, more preferably from about 40 to about 500 µm, even more preferably from about 50 to about 250 µm, and most preferably from about 50 to about 150 µm. The aspect ratio of the penetrator is ratio of the height divided by the average width of the penetrator. The average width of the penetrator is measured by taking the average width of the cross-sections of the penetrator at its base perpendicular to the height. The penetrator(s), preferably, has an aspect ratio of less than about 5, more preferably of less than about 2, even more preferably of less than about 1.5 and most preferably of less than about 0.75. The slope of the edge(s) or side(s) of the penetrator is measured by drawing a line tangent to the edge or the side of the penetrator(s) at any given point to the substrate and measuring the angle between the line and where it intersects the upper surface of the substrate. While it is understood that the slope may or may not vary substantially along the edge or side of the penetrator(s), preferably the slope is less than about 80 degrees over substantially all of the edge or side of the penetrator, more preferably is less than about 70 degrees, and most preferably is less than about 60 degrees. By substantially all of the edge or side of the penetrator, it is meant that 60% of the length of the edge or side has a slope less than that set forth above. However, preferably, 75% of the length of the edge or side has a slope of less than that set forth and more preferably 90% of the length of the edge or side has a slope of less than that set forth.

The epidermis or epidermal stop(s) of the present invention is a structure or elevation. Epidermis or epidermal stops are structures of a particular height with respect to the height of the penetrator(s) or other surface features so as to prevent the penetrator(s) or other surface features from unduly penetrating into the dermis of the skin or distorting the surface of the skin, respectively, where they might cause discomfort to the subject. An epidermis or epidermal stop(s) may also be incorporated into a penetrator, ridge, column, or like surface feature or can be a separate surface feature. Further preferably, the distance between the adjacent epidermal stops and penetrator(s) or surface features or adjacent penetrators or surface features is at least 80 µm at their nearest points, more preferably at least 160 µm and most preferably at least 250 µm. The epidermal stops may, however, have any shape known to those skilled in the art that would effectively prevent the penetrator(s) from entering the dermis of the skin. Furthermore, the epidermal stops are preferably applied in an array between the penetrators, therefore further minimizing inadvertent deep penetration or over penetration by the penetrator(s) or minimizing significant distortion of the skin by other surface structures. If the epidermal stop is a separate surface feature, preferably, the epidermal stop in combination with at least one other surface feature creates a detritus trough.

A detritus trough is the area interposed between adjacent surface structures or features. These troughs allow for a more accurate placement of the surface features by allowing for displacement or movement of the hair and other detritus on the skin in these troughs. Preferably, the detritus troughs are sufficient in number and size to allow for placement of the device on skin with a significant amount of hair such as for example the scalp or the chest of a male subject. Detritus troughs are created to maximize the area available for optimal device to skin contact, by improving the probability that hair and other detritus will enter the troughs and not preventing the surface features from either coming in contact with the skin or penetrating the skin.

The anchor(s) of the present invention is a structure or elevation that stabilizes the physiological device against a subject's skin. This stabilization further preferably prevents, or reduces, motion artifacts in the electrophysiological signal from the device, or any substantial movement. Motion artifacts that are generated in biopotential electrodes are induced by disrupting the electrical paths due to slipping, as well as by disturbance of the electrical double layer at the interfaces. The anchors reduce the chances for movement, and/or separation from the subject's skin. While the anchor can also be any of the structures described above, the anchor also can serve no other purpose except to stabilize or reduce movement of the device on the subject's skin. The anchor(s) can have a variety of cross sections over a length, all described above.

It is understood that the physiological recording devices of the present invention may have a combination of the various surface features described above. Various specific embodiments for the present invention are described as follows: In one embodiment, the present invention includes a physiological recording device comprising a substrate having an upper and a lower surface, and at least one ridge(s) formed on the lower surface, having a length, width, and height, wherein the ridge(s) depresses or pierces the stratum corneum or outer layer of the skin, and is capable of transmitting an electric potential that can be measured from the skin through the ridge(s).

In another embodiment, the present invention includes a physiological recording device comprising a substrate having an upper and a lower surface, at least one ridge(s) formed on the lower surface, and at least one penetrator wherein the penetrator is capable of depressing or piercing through the stratum corneum or outer layer of the skin, the ridge(s)

pierces or depresses the stratum corneum or outer layer of the skin, and both the penetrator and ridge in combination are capable, at least in part, of transmitting an electric potential that can be measured from the skin.

In another embodiment, the present invention includes a physiological recording device comprising a substrate having an upper and a lower surface, and at least one ridge formed on the lower surface, the cross section of the at least one ridge at least in part forms an arc wherein the ridge(s) depresses and/or pierces the stratum corneum or outer layer of the skin and is capable, at least in part, of transmitting an electric potential that can be measured from the skin through the ridge(s).

In another embodiment, the present invention includes a physiological recording device comprising a substrate having an upper and a lower surface, and at least one ridge formed on the lower surface, the cross section of the at least one ridge at least in part forms a trapezoid wherein the ridge(s) depresses and/or pierces the stratum corneum or outer layer of the skin, and is capable, at least in part, of transmitting an electric potential that can be measured from the skin through the ridge(s).

In another embodiment, the present invention includes a physiological recording device comprising a substrate having an upper and a lower surface, and at least one ridge formed on the lower surface, the cross section of the at least one ridge at least in part forms a triangle wherein the ridge(s) depresses and/or pierces the stratum corneum or outer layer of the skin, and capable, at least in part, of transmitting an electric potential that can be measured from the skin through the ridge(s).

In still another embodiment, the present invention includes a physiological recording device comprising a substrate having an upper and a lower surface, and at least one ridge formed on the lower surface, the cross section of the at least one ridge at least in part forms cup-like, parabolic end comprising two outer points and an inner bowl wherein the ridge(s) depresses and/or pierces the stratum corneum or outer layer of the skin, and capable, at least in part, of transmitting an electric potential that can be measured from the skin through the ridge(s).

In still another embodiment, the present invention includes a physiological recording device comprising a substrate having an upper and a lower surface, the lower surface of the substrate being substantially convex and at least one structure being formed on the lower surface, wherein the structure is capable, at least in part, of transmitting an electric potential that can be measured from the skin.

In even still another embodiment, the present invention includes a physiological recording device comprising a substrate having an upper and a lower surface, the lower surface of the substrate being substantially concave and at least one structure being formed on the lower surface, wherein the structure is capable, at least in part, of transmitting an electric potential that can be measured from the skin.

In still another embodiment, the present invention includes a physiological recording device comprising a substrate having an upper and a lower surface, the lower surface of the substrate being substantially curved and at least two structures being formed on the lower surface, the at least two structures both having different heights and/or shapes, wherein the at least two structures are capable, at least in part, of transmitting an electric potential that can be measured from the skin.

In still another embodiment, the present invention includes a physiological recording device comprising a substrate having an upper and a lower surface, the lower surface of the substrate not being substantially convex, concave, or flat, but rather is neither uniform nor substantially symmetric, and at least two structures being formed on the lower surface, the at least two structures both having different heights and/or shapes, wherein the at least two structures are capable, at least in part, of transmitting an electric potential that can be measured from the skin.

In still another embodiment, the present invention includes a physiological recording device for measuring physiological signals from the skin of subject comprising a substrate having an upper and a lower surface, and at least one structure being formed on the lower surface, wherein the at least one structure does not readily pierce the skin of the subject, assists in anchoring the physiological recording device to the skin of the subject and is capable, at least in part, of transmitting an electric potential from the skin that can be measured.

The penetrating recording device, and in particular one specific embodiment, the physiological electrode of the present invention, can be formed from a variety of processes and materials known to those skilled in the art. The substrate from which the penetrators or other surface features are formed or to which they are added can by way of example but not limitation be made from the following: conductive metal sheet and conductive metals including for example stainless steel, nickel and copper; semi-conductive metal including for example silicon and doped silicon wafers; ceramics including for example oxides; and polymers including for example electrically insulating polymers such as polyimides. Preferably, all non-conductive substrates are coated or doped to make the substrate semi-conductive or conductive. There are in general four processes by which embodiments of the present invention are preferably manufactured.

The first, and most preferable, process is where the electrode is formed by injection molding, casting or depositing a material into a mold to produce a dry electrode that is comprised of single piece construction, or optionally multiple piece construction. Another process that may be used is where the lower surface of the electrode is formed by replication techniques such as using a replication roll, which forms the negative image of the desired surface features of the lower surface of the electrode or by stamping or pressing different materials. In replication, a web of polymer material in the form of sheet or film is heated to soften the material and then passed over or under a replication roll to form the desired surface features of the lower surface of the device or electrode, generally, hundreds to thousands to possibly even millions of times over the length of the web of polymer material. The replicating roll is either internally cooled causing the web to re-harden during replication, or the web of polymer material is cooled to re-harden the polymer material after replication but prior to re-winding the web. In replication, the replicator could also be heated to allow for modifying the polymer material. The replicator processed web of polymer material can then be diced or sliced at some point into individual pieces, which form the lower surface of the physiological recording device or electrode. Similarly, the lower surface of devices or electrodes can be stamped or pressed from polymer sheet or polymer powders respectively. In the case of stamped devices or electrodes, a polymer sheet material is drawn to create the surface features. In the case of pressed devices or electrodes, polymer powders are pressed then sintered.

Preferably, the mold, replication or embossing method of the present invention also includes a method to roughen the surface of the electrode or device surface. Roughening of the surface of the mold or a replicating roll can be accomplished for example by shot peening the surface. Shot peening is the use of hardened balls or materials which are impacted against the surface to not only create roughening but to strengthen the surface. More preferably, a #30 glass impact bead is used to shot peen the surface of the mold. By roughening the surface of the mold, the electrodes or devices formed in the mold have a likewise roughened surface. This not only improves the adhesion of an adhesive collar used about the neck of the electrode or device, but also creates an electrode or device that will better anchor to the subject. The electrode or device could also be roughed by abrading or roughening the molded or replicated surface.

Preferably, the device or electrode is formed using an injection molding technique. The injection mold is preferably formed from a metal, more preferably, the mold has porous mold inserts in the areas requiring fine detail, and most preferably the sintered or other types of porous mold inserts are made out of materials such as Porcerax II. These sintered porous materials have a system of interconnected pores dispersed throughout the material. These types of materials, when used in appropriate areas, eliminates gas buildup, reduces injection pressure, lowers cycle times, gloss levels and substantially reduces scrap and reject rates. This type of sintered mold insert also allows for the production of the very fine micro-features or surface structures that populate the device or electrode's lower surface by allowing for the removal of air from the mold when creating these features. Porcerax II is a sintered porous metal with porosity in the range of 20 to 30% by volume, and requires complex machining, polishing, cleaning, and maintenance. These inserts help to eliminate trapped gases allowing for better venting within the mold. By proper design of the mold with the proper inserts and vent lines the devices or electrodes can be made without burning, shrinkage, short shots and improved appearance. These inserts also allow for a dull matte finish leading to better performance of the devices or electrodes in their application to the subject's skin. Preferably, the inserts have a pore size from about 5 to about 30 microns, a porosity of from about 15 to about 35% by volume, and a linear expansion which makes it compatible with the rest of the mold over the temperature range of the materials being molded. In forming while grinding and/or milling may be used, a method know as stoning which uses a back and forth or side to side method is used to remove metal that is crushed over the pores and to re-establish permeability or even more preferably a method known as electric discharge machining is used to re-establish permeability. Preferably, also the porous insert is connected to an exhaust line which facilitates the removal of gases from the mold cavity through the inserts during the molding process.

The mold is designed such that the imprint, or negative image, of the desired surface features that may include the penetrators, anchors, ridges, columns, detritus troughs, epidermal stops, and combinations thereof are formed to allow the substantial escape of gas during the molding process in the areas where these micro-features are formed. The injection mold may also require a core pin to mold the undercut of the snap stud in once piece, if a snap stud is the method of connection. The snap stud feature is created to maintain compatibility with most existing electrode snap connectors. As described later, however, there are other embodiments that are contemplated which allow for other types of connection of the devices or electrodes of the present invention with connecting wires or leads. The mold may be filled via injection molding, casting, deposition or other material forming technique to produce the desired device or electrode. Preferably, the material that actually forms the device or electrode is a polymer, more preferably the material is a thermoplastic, still more preferably the material is a liquid crystal polymer resin, and even more preferably the material is ABS. ABS is a material that offers unique combinations of toughness, stiffness, low mold shrinkage, and excellent flow properties which are all essential for the production of micro-features.

Once formed, the devices or electrodes are ejected and cooled. The device or electrode is then trimmed to remove any imperfections or to impart any device or electrode characteristics, which cannot be obtained through molding. Optionally, and as a function of the conductivity of the material utilized, the surface may be further doped to increase the conductivity of the device or electrode surface or of just the surface features, and also various film layers and leads can be coated onto the device or electrode to make it individually addressable or to function as desired in an array of electrodes. Preferably, the electrode is coated with a conductive metal surface via physical vapor deposition (PVD), or sputtering. The deposition material, silver or gold, is transferred to the substrate material with such energy as to cause the metal to intermingle with the substrate at the atomic level. More preferably, however, the electrode is coated with an electroplating technique using silver or gold coatings. Even more preferably, the electrode is coated with silver-silver chloride (Ag/Ag—Cl) which results in a non-polarizable electrode with better ohmic behavior and greater electrical stability (less noise). In coating the electrode with silver-silver chloride a standard electroplating process is used. The electrodes after coating, however, are not polished, which maintains a roughened surface thereby improving skin surface contact, and if an adhesive collar is used adhesion of the collar to the surface of the electrode.

A second general method of processing the device or electrode is by forming the device or electrode from silicon wafers. In the first step of this process, an oxide layer is formed on the silicon wafer. Following growth of the oxide layer, a photo resist (not shown) is applied and the pattern for the major surface features is transferred using a conventional photo resist process. Following application of the photo resist, the wafers etched to form the surface features. If epidermis stops are not desired then further etching of the wafer takes place to form the desired surface features. If, however, epidermis stops are desired, following the anisotropic etch, the surface of the silicon wafer is stripped of all oxides and masking material. Again, another oxide layer is formed on the silicon wafer. Following the growth of the oxide layer, a fairly thick photo resist is applied to the upper surface of the silicon wafer. Again, the photo resist is masked with a pattern but this time for the epidermis stops. Then a second bulk anisotropic etch is used to form the epidermis stops and to finish the surface features. After etching is completed, the remaining oxide is removed. At this point, the silicon optionally can be doped to increase the conductivity of the electrode, and also various film layers and leads can be coated onto the electrode to make surface features individually addressable or to function as desired in an array of electrodes.

A third general process for forming the device or electrode is by an additive deposition process. Preferably, an electroplating process is used. Preferably, the substrate for this process is a flexible polymer, and more preferably an insulating polymer such as a polyimide. With this process a thin layer of metal is applied to the substrate. Then, a thick layer of photo resist is applied to the thin layer of metal on the substrate and patterned by photolithography to create the desired surface features. These patterns form the base of the device or electrodes and the various surface features of the device or electrode. The photo resist is stripped from the substrate. Another layer of photoresist is applied. These patterns further define the surface structure which is built up to the desired height and shape by electroplating. Optionally, at this point various film layers and leads can be coated onto the electrode to make the surface features individually addressable or to function to improve the conductivity as desired in an array of electrodes.

Finally, a fourth process, for forming the device or electrode is from a metal sheet through photo micro-machining techniques. These techniques can be used to form the penetrator(s), ridges, anchors, columns, (epidermal stops, detritus troughs and springs, if desired), and combinations thereof. With this process one edge of a thin gauge stock of metal, preferably stainless steel, is photo defined and chemically etched, effectively forming a thin cross section of a desired two dimensional surface containing at least one of the above surface features described above. At this point various film layers, specific coatings and leads can be coated or deposited onto the electrode to make it individually addressable or to function as desired in an array. This forms a device or electrode with a cross section with approximately the thickness of the thin gauge metal stock. Stainless steel is preferred because of its good biocompatibility, excellent corrosion resistance, and because of its ability to be cleaned and reused, however, a variety of other materials known in the art can also be used. A device or electrode array can be formed by stacking or laminating many of these thin strip electrodes together. Additionally, laser machining, abrasion and other metal working techniques may be used to produce the electrode.

Preferably, the devices or electrodes of the present invention are of a monolithic design. That is the electrical connector of the device or electrode is incorporated by molding or other manufacturing process into the same substrate in which the surface features are part of. This monolithic or one piece design creates an electrode or device with better signal The devices or electrodes of the present invention can be used in a variety of applications including for measuring various biopotentials including but not limited to ECG, EEG, EMG, and EOG, and for taking other physiological measurements that can be determined from the skin or subcutaneous layers of the subject. The physiological recording electrode or device can be packaged by conventional packaging techniques, however, preferably the package provides 1) adequate structural support for the electrode so it can be handled roughly (i.e., dropped, crushed, etc) without damage; 2) a means (e.g., tape, belt or spring) preferably, to force the electrode or device against the subjects skin with a consistent pressure; 3) a low impedance path from the electrode's or device's surface to the package's output connector, and 4) a design which allows for easy cleaning and sterilization for applications requiring reuse. These electrode or device packages also can be mounted to the skin using conventional techniques such as adhesives, harnesses or bands.

The devices or physiological recording electrodes are applied to a subject, which can be an animal or human body having skin comprising an epidermis comprising a stratum corneum layer and lower layers of the epidermis, and a dermis. The ridge(s), column(s), and/or penetrator(s), in particular, of the device or electrode can anchor the device to or pierce through the stratum corneum layer of the skin with the penetrator(s) such that the penetrator(s) does not enter the dermis of the skin. The surface structures increase the surface contact with the skin and transforms a portion of the ionic current into an electric voltage that can be transmitted through these individual surface features.

The devices or electrodes of the present invention can have various types of connectors formed on the top or upper surface of the device or electrode. The connector can simply be a common button type connection in order to connect to standard terminals for various devices or can be shaped to provide for unique connecting features in order to require special terminals to be created for the monitoring device.

The ridges, columns and penetrators also increase the amount of surface area of the skin in contact with the device or electrode, which is applied. Preferably, the combination and the detail of the elevated surface structures increases the surface area of the lower surface of the device or electrode by at least 25%, more preferably by at least 50%, even more preferably by at least 75%, even more preferably by at least 150%, still more preferably by at least 250% and most preferably by at least 400%. This allows for greater pick up of (or stronger) signals from the skin's surface, and further allows for the device or electrode to be better anchored to the subject's skin resulting in less artifacts to the signal through movement and the like. The electric voltage from these surface features is measured using conventional measuring devices.

The Applicants herein incorporate by reference the disclosures of U.S. patent application Ser. Nos. 11/454,520, 10/988,358 and 11/401,559.

FIG. 2 is a cross-sectional view of the epidermis layer and an illustration of the insertion of the penetrator(s) of the present invention into the epidermis layer. The physiological recording electrode 10 is comprised of a substrate 12 having an upper surface 14 and a lower surface 13. The lower surface 13 of the substrate 12 comprising at least one penetrator(s) 16 sized and shaped for piercing the stratum corneum or outer layer of the epidermis, and accessing the lower layers of the epidermis. The penetrator 16 can take many shapes including but not limited to pyramidal, needle-like, triangular, or any other shape that can be tapered to a point or tip. Preferably, the size and shape of the penetrator 16 is such that the penetrator(s) 16 will not break or bend during normal use, will limit the depth the penetrator enters the skin under typical application conditions, and/or will anchor the electrode 10 to prevent motion artifacts or any substantial movement. Therefore, preferably, the appropriate aspect ratio of the height to the average width of the penetrator 16, slope of the edge(s) or side(s) of the penetrator 16, and/or height of the penetrator 16 are selected to make an electrode 10 wherein the penetrator(s) 16 will not break or bend, and will better anchor the electrode 10 during application. The height of the penetrator(s) is measured from the tip of the penetrator 16 perpendicular to the substrate 12.

FIGS. 3-24 show various specific embodiments of the present invention, including mainly different examples of the variations in the surface features, the variations of the surface shapes and combinations thereof.

Referring now to the attached figures, FIG. 3 is an isometric view of the upper surface of a device or an electrode 10. The device or electrode 10 is comprised of a substrate 12 having a upper 14 and lower 13 surfaces (the edge of which is shown). The lower surface 13 of the device or electrode has a connector 18 and a base 20 for the connector which provides structural support for both the connector 18 and the electrode's 10 structural or upper surface 14. The connector 18 in this particular embodiment is a button type of connector, which connects to standard leads used with electrodes or similar devices. The connector 14, however, can be snap type of electrode formed from a variety of shapes as mentioned earlier, can be a surface to which a lead can be mechanically attached by other devices, can be a surface to which a lead can be bonded or can be a surface to which any of a number of standard types of leads can be attached.

FIG. 4 is an isometric view highlighting the lower surface 13 of one embodiment of an electrode 10. The electrode 10 in FIG. 4 is shown with four rows of penetrators 16 that are pyramidal in shape on a flat lower surface 13 of the electrode 10. The flat lower surface 13 is preferably used when attaching the electrode to a location on a subject that is not rounded or bony, for example like the chest, back, stomach, or portions of the extremities of a subject.

FIG. 5 is a side view of an electrode 10 with a convex lower surface 13. The electrode comprises a substrate 12 with an lower 13 and upper 14 surfaces. A base for the connector 20 is on the upper surface 14. A standard snap type connector 18 is attached to the base 20. The electrode 10 is populated with penetrators 16 on the lower surface 13 which are needle-like in shape, and generally are approximately the same height. The convex nature of the electrode's lower surface 22 may aid in application of the electrode 10 to an area on a subject that is depressed such as areas near the sternum, armpit and the like. Preferably, penetrators 16 on such a device or electrode 10 are of such height that the points of their tips if connected would form a curve that is generally parallel to the curvature of the lower surface 13.

FIG. 6 is a side view of another embodiment of a physiological recording electrode 10. The electrode 10 comprises a substrate 12 with an lower 13 and upper 14 surfaces. A base for the connector 20 is on the upper surface 14. A standard snap type connector 18 is attached to the base 20. The electrode 10 has a convex lower surface 13 populated with penetrators 16 that are needle-like in shape, and varying in height in proportion to the curvature of the surface so that their tips all are points that if connected would approximate a straight line. This embodiment of the present invention may aid in application to a flat area on the subject's body such as the chest, back, or stomach.

FIG. 7 is a side view of another embodiment of a physiological recording electrode 10. The electrode 10 comprises a substrate 12 with an upper 14 and lower surface 13. A base for the connector 20 is on the upper surface 14. A standard snap type connector 18 is attached to the base 20. The electrode 10 has a concave lower surface 13 populated with penetrators 16 that are approximately the same height, so that their tips all are points that if connected would form a curve that is substantially parallel to the curvature of the lower surface 13. This also may aid in the application of the electrode to a curved or bony area on the subject's body such as a wrist, a finger, ankle, or knee.

FIG. 8. is a side view of another embodiment of a physiological recording electrode 10. The electrode 10 comprises a substrate 12 with an upper 14 and lower surface 13. A base for the connector 20 is on the upper surface 14. A standard snap type connector 18 is attached to the base 20. The electrode 10 has a concave lower surface 13 populated with penetrators 16 that are pyramidal in shape and are varying in height in proportion to the curvature of the upper surface 13 so that their tips all are points that if connected would form or approximate a straight line. This embodiment of the present invention may also aid in application to a flat area on the subject's body such as their chest, back, or stomach.

FIG. 9. is a side view of another embodiment of a physiological recording electrode 10. The electrode 10 comprises a substrate 12 with an upper 14 and lower surface 13. A base for the connector 20 is on the upper surface 14. A standard snap type connector 18 is attached to the base 20. The electrode 10 has a convex lower surface 13 populated with penetrators 16 that are needle-like in shape, ridges 24 with a height slightly lower than the penetrators 16, and epidermal stops 22 that are significantly shorter than the height than the penetrators 16. The penetrators 16 readily pierce the skin, but are limited as to how deep they can penetrate into the skin by both the epidermis stops 22 and the ridges 24. The ridges 70 further depress the subject's skin allowing for greater surface contact and acting further to limit the depth of penetration of the penetrators 16. The ridges 24 have a trapezoidal cross section and extend over length (not shown).

FIG. 10 is a side view of another embodiment of a physiological recording electrode 10. The electrode 10 comprises a substrate 12 with an upper 14 and lower surface 13. A base for the connector 20 is on the upper surface 14. A standard snap type connector 18 is attached to the base 20. The electrode 10 has a convex lower surface 22 populated with columns 26 that are approximately the same height, and have a slightly tapered edge 28. The columns 26 depress the subject's skin increasing the surface area of the upper surface 13 of the electrode 10 in contact with the subject's skin, but may not pierce or penetrate the skin.

FIG. 11 is a side view of another embodiment of a physiological recording electrode 10. The electrode 10 comprises a substrate 12 with an upper 14 and lower 13 surfaces. A base for the connector 20 is on the upper surface 14. A standard snap type connector 18 is attached to the base 20. The electrode 10 has a flat lower surface 13 populated with penetrators 16 that are pyramidal in shape and vary in height to form a dome-like shape of penetrator 16 tips.

FIG. 12 is an isometric view of another embodiment of a physiological recording electrode 10. The electrode 10 comprises a substrate 12 with an upper 14 and lower 13 surfaces. A base for the connector 20 is on the upper surface 14. A connecting surface 18 is attached to the base 20. The electrode 10 has on its flat lower surface 13 with a spiral arrangement or pattern 28 of penetrators 16. The details of the penetrators 16 are better viewed in the call out 30, which shows a pyramidal shaped penetrators 16.

FIG. 13 is an isometric view of another embodiment of a physiological recording electrode 10. The electrode 10 comprises a substrate 12 with an upper 14 and lower 13 surfaces. A base for the connector 20 is on the upper surface 14. A connecting surface 18 is attached to the base 20. The electrode 10 has on its flat lower surface 13 concentric rings or a circular arrangement or pattern 32 of ridges 24. The details of the ridges 24 are better viewed in the call out 30, which shows a ridge 24 with a trapezoidal cross section 34 over a length of a ridge 36. The concentric arrangement of rings enhance the electrode-skin interface, and improve subject comfort by creating space for hair, detritus, air, and/or moisture to flow or collect.

FIG. 14 a) is an isometric view of another embodiment of a physiological recording electrode 10. The electrode 10 comprises a substrate 12 with an upper 14 and lower 13 surfaces. A base for the connector 20 is on the upper surface 14. A connecting surface 18 is attached to the base 20. The electrode 10 has on its flat lower surface 13 five straight ridges 24 extending over a length 36. The details of the ridges 24 are better viewed in the call out 30, which shows a ridge 24 with a trapezoidal cross section 34 over a length of a ridge 36. The linear spacing of the ridges 24 also enhances the electrode-skin interface, and improves subject comfort by creating space or detritus trough 38 for hair, detritus, air, and/or moisture to flow or collect.

FIG. 14 b) is an isometric view of another embodiment of a physiological recording electrode 10. The electrode 10 comprises a substrate 12 with an upper 14 and lower 13 surfaces. A base for the connector 20 is on the upper surface 14. A connecting surface 18 is attached to the base 20. The electrode 10 has on its flat lower surface 13 twelve groupings of a first ridge 24 perpendicularly positioned with respect to a second ridge 25. The details of the ridges 24, 25 are better viewed in the call out 30, which shows a ridges 24, 25 with trapezoidal cross sections 34 over a length of a ridge 36. The linear and perpendicular spacing/placement of the ridges 24, 25 also enhances the electrode-skin interface, and improves subject comfort by creating space or detritus trough 38 for hair, detritus, air, and/or moisture to flow or collect.

FIG. 15 is an isometric view of another embodiment of a physiological recording electrode 10. The electrode 10 comprises a substrate 12 with an upper 14 and lower 13 surfaces. A base for the connector 20 is on the upper surface 14. A connecting surface 18 is attached to the base 20. The electrode 10 has on its flat lower surface 13 non-continuous concentric rings or a circular arrangement or pattern 32 of ridges 24. The details of the ridges 24 are better viewed in the call out 30, which shows a ridge 24 with a triangular cross section 40 over a length of a ridge 36. The non-continuous concentric arrangement of rings enhances the electrode-skin interface, and improves subject comfort by creating space or a detritus trough 38 for hair, detritus, air, and/or moisture to flow or collect.

FIG. 16 is an isometric view of another embodiment of a physiological recording electrode 10. The electrode 10 comprises a substrate 12 with an upper 14 and lower 13 surfaces. A base for the connector 20 is on the upper surface 14. A connecting surface 18 is attached to the base 20. The electrode 10 has four varying topographic regions or multiple surface structures 42 on it's lower surface 13. The call out of the multiple surface structure regions 42 shows pyramidal penetrators 16 in one region, ridges 24 in another region, thatch-like or double penetrators 17 in another region, and a combination of ridges 24, penetrators 16 and epidermal stops 22 in another region in quadrants 44 on the electrode's 10 flat upper surface 13. The arrangement of varying surface features enhance the electrode-skin interface, lowers the impedance and improve the subject's comfort by creating space or a detritus trough 38 for hair, detritus, air, and/or moisture to flow or collect.

FIG. 17 is a side view of another embodiment of a physiological recording electrode 10. The electrode 10 comprises a substrate 12 with an upper 14 and lower 13 surfaces. A base for the connector 20 is on the upper surface 14. A standard snap type connector 18 is attached to the base 20. The electrode 10 has a flat lower surface 13 populated with thatch-like or double penetrators 17. The call out 30 shows in greater detail the features of the thatch-like or double penetrators 17.

FIG. 18 is an isometric view of another embodiment of a physiological recording electrode 10. The electrode 10 comprises a substrate 12 with an upper 14 and lower 13 surfaces. A base for the connector 20 is on the upper surface 14. A connecting surface 18 is attached to the base 20. The electrode 10 has various raised surface features 46 on the lower surface 13 in an almost L-shape. These raised surface features are interlocking columns 26. The other raised surface features having a height (not shown).

FIG. 19 is an isometric view of another embodiment of a physiological recording electrode 10. The electrode 10 comprises a substrate 12 with an upper 14 and lower 13 surfaces. A base for the connector 20 is on the upper surface 14. A connecting surface 18 is attached to the base 20. The electrode 10 has a large number of columns 26 on the lower surface 13. These columns 26 are shown in more detail in the call out 30. In the call out 30, the columns 26 have a concave or cup end 48 with two micropenetrators 50. The arrangement of cup-ended columns enhances the electrode-skin interface, and improves subject comfort by creating space or a detritus trough (not shown) for hair, detritus, air, and/or moisture to flow or collect.

FIG. 20 is an isometric view of another embodiment of a physiological recording electrode 10. The electrode 10 comprises a substrate 12 with an upper 14 and lower 13 surfaces. A base for the connector 20 is on the upper surface 14. A connecting surface 18 is attached to the base 20. The electrode 10 with trapezoidal columns 26 on its flat lower surface 13 arranged in clusters with channels 52. The arrangement of clustered columns enhance the electrode-skin interface, and improve subject comfort by creating space or a detritus trough 38 for hair, detritus, air, and/or moisture to flow or collect.

FIG. 21 is an isometric view of another embodiment of a physiological recording electrode 10. The electrode 10 comprises a substrate 12 with an upper 14 and lower 13 surfaces. A base for the connector 20 is on the upper surface 14. A connecting surface 18 is attached to the base 20. The electrode 10 as shown in the cutout 30 with triangular ridges 24 on its flat lower surface 13 arranged in a seven small rings 54. The arrangement of seven small rings 54 enhances the electrode-skin interface, and improves subject comfort by creating space or a detritus trough 38 for hair, detritus, air, and/or moisture to flow or collect.

FIG. 22 is an isometric view of another embodiment of a physiological recording electrode 10. The electrode 10 comprises a substrate 12 with an upper 14 and lower 13 surfaces. A base for the connector 20 is on the upper surface 14. A connecting surface 18 is attached to the base 20. The electrode 10 as shown in the callout 30 with triangular ridges 24 on its flat lower surface 13 arranged in non-concentric rings 56. The arrangement of non-concentric rings 56 shown better in the callout 30 enhances the electrode-skin interface, and improves subject comfort by creating space or a detritus trough 38 for hair, detritus, air, and/or moisture to flow or collect.

FIG. 23 is an isometric view of another embodiment of a physiological recording electrode 10. The electrode 10 comprises a substrate 12 with an upper 14 and lower 13 surfaces. A base for the connector 20 is on the upper surface 14. A connecting surface 18 is attached to the base 20. The electrode 10 is shown in the callout 30 with columns 26 with pyramidal caps 58 on its flat lower surface 13. The arrangement of pyramidal columns shown better in the callout 30 enhances the electrode-skin interface, and improves subject comfort by creating space or a detritus trough 38 for hair, detritus, air, and/or moisture to flow or collect. These columns 26 do not easily pierce the skin, like a pyramidal penetrator, but rather merely depress the skin to anchor the electrode.

FIG. 24 is an isometric view of another embodiment of a physiological recording electrode 10. The electrode 10 comprises a substrate 12 with an upper 14 and lower 13 surfaces. A base for the connector 20 is on the upper surface 14. A connecting surface 18 is attached to the base 20. The electrode 10 as shown in the callout 30 with penetrators 16 that are pyramidal in shape on its flat upper surface 13 arranged in clusters with channels 52 on the electrodes lower surface 13. The arrangement of clustered penetrators enhances the electrode-skin interface, and improves subject comfort by creating space or a detritus trough 38 for hair, detritus, air, and/or moisture to flow or collect.

It will be apparent to those skilled in the an that various modifications and variations can be made to the present invention without departing from the spirit and scope of the invention. Thus, it is intended that the present invention cover the modifications and variations of this invention provided they come within the scope of the appended claims and their equivalents.

We claim:

1. A physiological recording device for a skin of a subject comprising:
    a monolithic thermoplastic electrode comprising a substrate having an upper and a lower surface, the lower surface of the substrate being a continuous concave curve over a majority of the lower surface, a plurality of elevated surface features on the lower surface of the substrate, a connector on the upper surface of the substrate, a conductive coating covering the plurality of elevated surface features and at least part of the lower surface of the substrate, and a low-impedance electrical pathway from the conductive coating to the connector,
    wherein the elevated surface features are adapted for depressing the skin, and, at least in part, transmitting an electric potential that can be measured from the skin.

2. The physiological recording device in claim 1, wherein at least one of the plurality of surface features is a penetrator wherein the at least one penetrator is capable of penetrating a stratum corneum or outer layer of the skin, and, also at least in part, of transmitting an electric potential that can be measured from the skin.

3. The physiological recording device in claim 1, wherein at least one of the plurality of surface features is a column or a ridge.

4. The physiological recording device in claim 1, wherein the connector is a male snap connector.

5. The physiological recording device in claim 1, wherein the conductive coating is a substantially uniform thickness covering the entire electrode.

6. The physiological recording device in claim 1, wherein the surface features increase the amount of surface area of the lower surface of the device in contact with the subject's skin by at least 100%.

7. The physiological recording device of claim 1, wherein the plurality of surface features comprises surface features of two or more types, each type having different heights and/or shapes.

8. A physiological recording device for a skin of a subject comprising:
    a monolithic thermoplastic electrode comprising a substrate having an upper and a lower surface, the lower surface of the substrate being a continuous concave over a majority of the lower surface, a plurality of elevated surface features on the lower surface of the substrate, a connector on the upper surface of the substrate, a conductive coating covering the plurality of elevated surface features and at least part of the lower surface of the substrate, and a low-impedance electrical pathway from the conductive coating to the connector,
    wherein the elevated surface features are arranged in a non-concentric pattern and are adapted for depressing the skin, and, at least in part, transmitting an electric potential that can be measured from the skin.

9. The physiological recording device of claim 8, wherein at least one of the plurality of surface features is a penetrator wherein the at least one penetrator is capable of penetrating a stratum corneum or outer layer of the skin, and, also at least in part, of transmitting an electric potential that can be measured from the skin.

10. The physiological recording device of claim 8, wherein the plurality of surface features comprises surface features of two or more types, each type having different heights and/or shapes.

11. The physiological recording device of claim 8, wherein the connector is a male snap connector.

12. The physiological recording device of claim 8, wherein the conductive coating is a substantially uniform thickness covering the entire electrode.

13. The physiological recording device of claim 8, wherein at least one of the plurality of surface features is a column or a ridge.

14. The physiological recording device of claim 8, wherein the surface features increase the amount of surface area of the lower surface of the device in contact with the subject's skin by at least 100%.

15. A physiological recording device for a skin of a subject comprising:
    a monolithic thermoplastic electrode comprising a substrate having an upper and a lower surface, the lower surface of the substrate being a continuous concave curve over a majority of the lower surface, a plurality of elevated surface features on the lower surface of the substrate, a connector on the upper surface of the substrate, a conductive coating covering the plurality of elevated surface features and at least part of the lower surface of the substrate, and a low-impedance electrical pathway from the conductive coating to the connector,
    wherein the elevated surface features do not readily pierce the skin of the subject, and are adapted, at least in part, for transmitting an electric potential that can be measured from the skin.

16. The physiological recording device of claim 15, the surface features increase the amount of surface area of the lower surface of the device in contact with the subject's skin by at least 100%.

17. The physiological recording device of claim 15, wherein the plurality of surface features comprises surface features of two or more types, each type having different heights and/or shapes.

18. The physiological recording device of claim 15, wherein the connector is a male snap connector.

19. The physiological recording device of claim 15, wherein the conductive coating is a substantially uniform thickness covering the entire electrode.

20. The physiological recording device of claim 15, wherein at least one of the plurality of surface features is a column or a ridge.

* * * * *